US012800572B2

(12) United States Patent
Williams

(10) Patent No.: US 12,800,572 B2
(45) Date of Patent: Nov. 17, 2026

(54) CELL-BASED ASSAY FOR DETERMINING THE IN VITRO TUMOR KILLING ACTIVITY OF CHIMERIC ANTIGEN EXPRESSING IMMUNE CELLS

(71) Applicant: Janssen Biotech, Inc., Horsham, PA (US)

(72) Inventor: J. Kendall Williams, West Chester, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 514 days.

(21) Appl. No.: 17/340,296

(22) Filed: Jun. 7, 2021

(65) Prior Publication Data

US 2022/0057381 A1 Feb. 24, 2022

Related U.S. Application Data

(60) Provisional application No. 63/125,173, filed on Dec. 14, 2020, provisional application No. 63/036,249, filed on Jun. 8, 2020.

(51) Int. Cl.
*G01N 33/50* (2006.01)

(52) U.S. Cl.
CPC ....... *G01N 33/505* (2013.01); *G01N 33/5017* (2013.01)

(58) Field of Classification Search
None
See application file for complete search history.

(56) References Cited

U.S. PATENT DOCUMENTS

| | | | | |
|---|---|---|---|---|
| 11,266,690 B2 * | 3/2022 | Zhou | .................. | C07K 14/7051 |
| 2020/0078399 A1 * | 3/2020 | Fan | .................... | A61K 2239/48 |

FOREIGN PATENT DOCUMENTS

| | | |
|---|---|---|
| WO | 2013126720 A2 | 8/2013 |
| WO | 2017025038 A1 | 2/2017 |
| WO | 2018028647 A1 | 2/2018 |
| WO | 2018111340 A1 | 6/2018 |
| WO | 2018156802 A1 | 8/2018 |
| WO | 2019090003 A1 | 5/2019 |
| WO | 2020051345 A1 | 3/2020 |
| WO | 2020092854 A2 | 5/2020 |
| WO | 2021250552 A1 | 12/2021 |

OTHER PUBLICATIONS

Hudecek M, Lupo-Stanghellini MT, Kosasih PL, Sommermeyer D, Jensen MC, Rader C, Riddell SR (2013) "Receptor affinity and Extracellular Domain Modifications affect tumor recognition by ROR1-specific Chimeric Antigen Receptor T cells", Clinical Cancer Research, 19, 12, pp. 3153-3164 (Year: 2013).*

Pont MJ, Hill T, Cole GO, Abbott JJ, Kelliher J, Salter Al, Hudecek M, Cosmstock ML, Rajan A, Patel BKR, Voutsinas JM, Wu Q, Liu L, Cowan AJ, et al. (2019) "Secretase inhibition increases efficacy of BCMA-specific chimeric antigen receptor T cells in multiple myeloma" Blood, 134, 19, pp. 1585-1597 (Year: 2019).*

Rotolo A, Karadimitris A, Ruella, M (2018) "Building upon the success of CART19: chimeric antigen receptor T cells for hematologic malignancies", Leukemia & Lymphoma, 59, 9, pp. 2040-2055 (Year: 2018).*

Bergeron et al. (2017) "CAR-T cell Screening in Tumor Spheroids using Corning® Spheroid Microplates and KILR® Cytotoxicity Assay" 4 pages, https://www.discoverx.com/content/uploads/2023/07/spheroid-kilr-car-t-assays_corning-discoverx-application-note_2017.pdf (Year: 2017).*

Wonderlich J, Shearer G, Livingstone A, Brooks A, Soloski MJ, Presby MM (2018) "Induction and Measurement of Cytotoxic T Lymphocyte Activity", Current Protocols in Immunology, 120, 1, pp. 3.11.1-3.11.29 (Year: 2018).*

Sommer C, Boldajipour B, Valton J, Galetto R, Bentley T, Sutton J, Ni Y, Leonard M, Van Blarcom T, Smith J, Chaparro-Riggers J. ALLO-715, an allogeneic BCMA CAR T therapy possessing an off-switch for the treatment of multiple myeloma. Blood. Nov. 29, 2018;132:591. (Year: 2018).*

Acro Biosystems, Product sheet, Human BCMA/TNFRSF17 protein, Catalog# BCA-H522y, Jun. 26, 2024 (Year: 2024).*

Linney ID, Kaila N. Inhibitors of immuno-oncology target HPK1-a patent review (2016 to 2020). Expert Opinion on Therapeutic Patents. Oct. 3, 2021;31(10):893-910. (Year: 2021).*

Akahori Y, Wang L, Yoneyama M, Seo N, Okumura S, Miyahara Y, Amaishi Y, Okamoto S, Mineno J, Ikeda H, Maki T. Antitumor activity of CAR-T cells targeting the intracellular oncoprotein WT1 can be enhanced by vaccination. Blood. Sep. 13, 2018;132(11):1134-45 (Year: 2018).*

(Continued)

*Primary Examiner* — Soren Harward
*Assistant Examiner* — Stefanie J. Kirwin
(74) *Attorney, Agent, or Firm* — TROUTMAN PEPPER LOCKE LLP

(57) ABSTRACT

The disclosure provides an in vitro method for determining potency (e.g., cytotoxicity) of an immune cell expressing a chimeric antigen receptor (CAR) molecule. In a test sample, CAR-expressing immune cells are incubated with target cells expressing an antigen which interacts with the CAR. In a control sample, the CAR-expressing immune cells are incubated with the target cells and an inhibitory molecule that prevents interaction between the CAR and the target cells. The amount of target cell death is determined in both the test sample and the control sample and is compared.

16 Claims, 1 Drawing Sheet

Specification includes a Sequence Listing.

(56) References Cited

OTHER PUBLICATIONS

International Search Report and Written Opinion for International Patent Application No. PCT/IB2021/054996 dated Jul. 30, 2021.
International Preliminary Report on Patentability issued Dec. 13, 2022 in International Application No. PCT/IB2021/054996.
Nonfinal Office Action for U.S. Appl. No. 17/340,296 dated Nov. 8, 2023.
Petukhov et al., "Manufacturing of CD19 Specific CAR T-Cells and Evaluation of their Functional Activity in Vitro," Clinical Oncohematology (2018) vol. 11, No. 1, pp. 1-9. (English abstract).
Berdeja et al., "Update of CARTITUDE-1: A phase 1b/2 study of JNJ-4528, a B-cell maturation antigen (BCMA)—directed CAR-T cell therapy, in relapsed/refractory multiple myeloma," Presented at the 56th Annual Meeting of the American Society of Clinical Oncology (ASCO) 2020, Virtual, May 29-31, 2020.

* cited by examiner

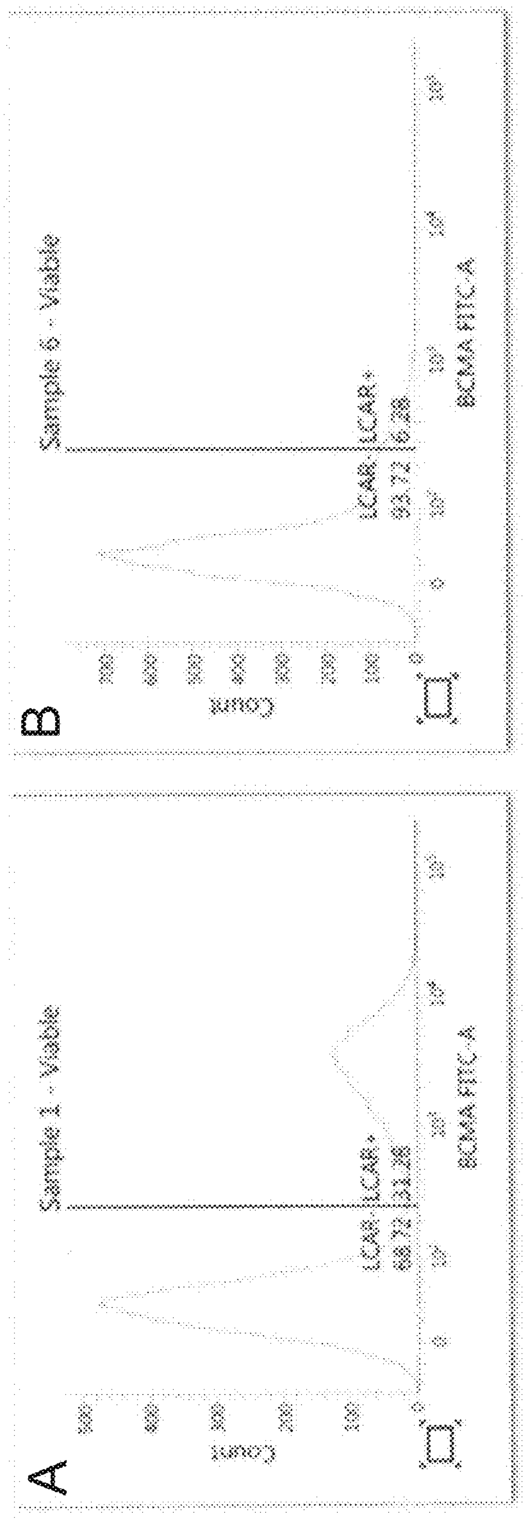
A
Sample 1 - Viable
LCAR-
68.72
LCAR+
31.28
Count
BCMA FITC-A
B
Sample 6 - Viable
LCAR-
93.72
LCAR+
6.28
Count
BCMA FITC-A

SEQUENCE LISTING

```
<160> NUMBER OF SEQ ID NOS: 12

<210> SEQ ID NO 1
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Ser Val Glu Ala Leu Asp Tyr Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190
```

```
Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445


<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Asp
            20                  25                  30

Leu Ala Trp Tyr Gln Gln Lys Pro Gly Gln Ala Pro Arg Leu Leu Ile
        35                  40                  45

Tyr Ile Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ile Arg Ala Pro Phe
                85                  90                  95

Thr Phe Gly Gln Gly Thr Lys Val Glu Ile Lys Arg Ala Asp Ala Ala
            100                 105                 110
```

```
Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 3
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Phe Pro Trp Asp Leu Ala Tyr Ala Leu Asp Tyr Trp
            100                 105                 110

Gly Gln Gly Thr Leu Val Thr Val Ser Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
```

-continued 245 250 255

Met Ile Ser Leu Ser Pro Ile Val Thr Cys Val Val Val Asp Val Ser
260 265 270

Glu Asp Asp Pro Asp Val Gln Ile Ser Trp Phe Val Asn Asn Val Glu
275 280 285

Val His Thr Ala Gln Thr Gln Thr His Arg Glu Asp Tyr Asn Ser Thr
290 295 300

Leu Arg Val Val Ser Ala Leu Pro Ile Gln His Gln Asp Trp Met Ser
305 310 315 320

Gly Lys Glu Phe Lys Cys Lys Val Asn Asn Lys Asp Leu Pro Ala Pro
325 330 335

Ile Glu Arg Thr Ile Ser Lys Pro Lys Gly Ser Val Arg Ala Pro Gln
340 345 350

Val Tyr Val Leu Pro Pro Pro Glu Glu Glu Met Thr Lys Lys Gln Val
355 360 365

Thr Leu Thr Cys Met Val Thr Asp Phe Met Pro Glu Asp Ile Tyr Val
370 375 380

Glu Trp Thr Asn Asn Gly Lys Thr Glu Leu Asn Tyr Lys Asn Thr Glu
385 390 395 400

Pro Val Leu Asp Ser Asp Gly Ser Tyr Phe Met Tyr Ser Lys Leu Arg
405 410 415

Val Glu Lys Lys Asn Trp Val Glu Arg Asn Ser Tyr Ser Cys Ser Val
420 425 430

Val His Glu Gly Leu His Asn His His Thr Thr Lys Ser Phe Ser Arg
435 440 445

Thr Pro Gly Lys
450

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Gly Asn Tyr
20 25 30

Leu Asn Trp Tyr Gln Gln Lys Pro Gly Lys Ala Pro Lys Leu Leu Ile
35 40 45

Tyr Asp Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Phe Pro Phe
85 90 95

Thr Phe Gly Gln Gly Thr Lys Val Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

```
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 5
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Ala Phe Ser Ser Tyr Ala Leu Asp Tyr Trp Gly Gln
            100                 105                 110

Gly Thr Leu Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285
```

Thr Ala Gln Thr Gln Thr His Arg Glu Asp Tyr Asn Ser Thr Leu Arg
290 295 300

Val Val Ser Ala Leu Pro Ile Gln His Gln Asp Trp Met Ser Gly Lys
305 310 315 320

Glu Phe Lys Cys Lys Val Asn Asn Lys Asp Leu Pro Ala Pro Ile Glu
325 330 335

Arg Thr Ile Ser Lys Pro Lys Gly Ser Val Arg Ala Pro Gln Val Tyr
340 345 350

Val Leu Pro Pro Pro Glu Glu Glu Met Thr Lys Lys Gln Val Thr Leu
355 360 365

Thr Cys Met Val Thr Asp Phe Met Pro Glu Asp Ile Tyr Val Glu Trp
370 375 380

Thr Asn Asn Gly Lys Thr Glu Leu Asn Tyr Lys Asn Thr Glu Pro Val
385 390 395 400

Leu Asp Ser Asp Gly Ser Tyr Phe Met Tyr Ser Lys Leu Arg Val Glu
405 410 415

Lys Lys Asn Trp Val Glu Arg Asn Ser Tyr Ser Cys Ser Val Val His
420 425 430

Glu Gly Leu His Asn His His Thr Thr Lys Ser Phe Ser Arg Thr Pro
435 440 445

Gly Lys
450

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 6

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ala Asp Phe
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Ser His Arg Ala Pro Phe
85 90 95

Thr Phe Gly Gln Gly Thr Lys Val Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr

```
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 7
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Ala Ile Ser Trp Val Arg Gln Pro Pro Gly Lys Gly Leu Glu Trp Leu
        35                  40                  45

Gly Val Ile Trp Thr Asp Gly Gly Thr Asn Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Arg Glu Asp Ser Tyr Gly Asp Leu Phe Ala Tyr Trp Gly Gln Gly
            100                 105                 110

Thr Thr Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320
```

Phe Lys Cys Lys Val Asn Asn Lys Asp Leu Pro Ala Pro Ile Glu Arg
325 330 335

Thr Ile Ser Lys Pro Lys Gly Ser Val Arg Ala Pro Gln Val Tyr Val
340 345 350

Leu Pro Pro Pro Glu Glu Glu Met Thr Lys Lys Gln Val Thr Leu Thr
355 360 365

Cys Met Val Thr Asp Phe Met Pro Glu Asp Ile Tyr Val Glu Trp Thr
370 375 380

Asn Asn Gly Lys Thr Glu Leu Asn Tyr Lys Asn Thr Glu Pro Val Leu
385 390 395 400

Asp Ser Asp Gly Ser Tyr Phe Met Tyr Ser Lys Leu Arg Val Glu Lys
405 410 415

Lys Asn Trp Val Glu Arg Asn Ser Tyr Ser Cys Ser Val Val His Glu
420 425 430

Gly Leu His Asn His His Thr Thr Lys Ser Phe Ser Arg Thr Pro Gly
435 440 445

Lys

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Asp Ile Val Met Thr Gln Ser Pro Ala Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Thr Asn Thr Trp Pro Leu
85 90 95

Thr Phe Gly Ala Gly Thr Lys Leu Glu Leu Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

<210> SEQ ID NO 9
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Trp Asp Leu Val Leu Ser Ile Ala Leu Ser Val Gly Cys Thr Gly
1               5                   10                  15

Ala Val Pro Leu Ile Glu Gly Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
    50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
                245                 250                 255

Ile Ala Ala Asn Pro His His His His His His
            260                 265
```

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30
```

-continued

```
Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 11
<211> LENGTH: 42
<212> TYPE: PRT
<213> ORGANISM: Unknown
<220> FEATURE:
<223> OTHER INFORMATION: Description of Unknown:
      4-1BB co-stimulatory domain or CD137 co-stimulatory domain
      sequence

<400> SEQUENCE: 11

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5
```

CELL-BASED ASSAY FOR DETERMINING THE IN VITRO TUMOR KILLING ACTIVITY OF CHIMERIC ANTIGEN EXPRESSING IMMUNE CELLS

CROSS-REFERENCE TO RELATED APPLICATIONS

This application claims the benefit of U.S. Provisional Application Ser. No. 63/036,249, filed 8 Jun. 2020 and U.S. Provisional Application Ser. No. 63/125,173, filed 14 Dec. 2020. The entire content of the aforementioned applications is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 4, 2021, is named JBI6329USNP1_SL.txt and is 28,445 bytes in size.

TECHNICAL FIELD

The invention provides for improved assays for determining potency (e.g., cytotoxicity) of immune cells expressing chimeric antigen receptors. The improved assays allow for avoiding use of a mock transfected immune cell as assay control, by instead using an inhibitory molecule that prevents the chimeric antigen receptor of the immune cell from interacting with its target cell as assay control.

BACKGROUND

Current methods of determining the specific in vitro cytotoxicity of T cells expressing chimeric antigen receptor (CAR-T cells) involve use of autologous un-transduced expanded T cells (mocks) as a baseline control. These controls are used to calculate the specific cytotoxicity of the transduced CAR-T cells. However, generation of un-transduced expanded autologous or allogenic control T-cells (mock cells) is expensive and time consuming, particularly because these cells are usually generated from the patient's own T cells. In addition, generation of the mock cells is prone to production failures, which can delay therapy or interfere with proper dosing of the CAR-T cells during immunotherapy.

Methods of determining the in vitro cytotoxicity of CAR-T cells involve the use of autologous un-transduced expanded T cells (mocks) as a baseline control. Baseline controls are used to calculate the percentage increase in cytotoxicity specific to the CAR-T cells (percentage CAR-T killing). If no autologous mock cells are available, qualified lots of allergenic mocks are used instead. However, use of such qualified lots results in a potency relative to the allogenic mocks that may not reflect the true potency of CAR-T cells. Alternatively, the baseline control is omitted, and the total cytotoxic activity is used. However, total cytotoxic activity does not indicate if there has been any enhancement in cytotoxic activity of the immune cell/target cell interaction due to the CAR-T cells. Total cytotoxic activity does not differentiate the contribution from the drug product, or spontaneous death of the target cells themselves. Alternative assays, such as cytokine ELISA, have been used in place of functional assays as a surrogate for measuring activity, but these methods are not a direct measurement of cytotoxicity.

Accordingly, there is a need for improved assay controls so as to simplify production and testing of CAR-T cells while preserving accuracy of CAR-T cell potency and while reducing the associated high costs and complexity associated with using mock cells and/or additional alternative assays when mock cells are not available. The subject matter described throughout this application meets this need by providing novel assays that do not require use of mock cells as controls.

SUMMARY OF THE INVENTION

In one aspect is provided an in vitro method for determining potency of an immune cell expressing a chimeric antigen receptor (CAR) molecule, the method comprising:

a) in a test sample, contacting the CAR-expressing immune cells with target cells, wherein the target cells express an antigen which interacts with the CAR,
b) in a first control sample, contacting the CAR-expressing immune cells with the target cells, wherein (i) said contacting is conducted in the presence of an inhibitory molecule or (ii) the CAR-expressing immune cells and/or the target cells have been pre-incubated with the inhibitory molecule prior to said contacting, wherein the inhibitory molecule inhibits interaction between the CAR and the target cells,
c) determining the amount of the target cell death in the test sample,
d) determining the amount of the target cell death in the first control sample, and
e) determining potency of CAR-expressing immune cells based on comparing the amount of the target cell death determined in steps (c) and (d), wherein the contacting time, the amount of the CAR-expressing immune cells and the amount of the target cells are substantially the same in the test sample and the first control sample.

In some embodiments, the contacting steps (a) and (b) are performed simultaneously. In some embodiments, the determining steps (c) and (d) are performed simultaneously.

In some embodiments, in step (b)(i) the CAR-expressing immune cells and/or the target cells have been pre-incubated with the inhibitory molecule prior to the contacting step.

In some embodiments, the method further comprises comparing the amount of the target cell death determined in step (c) to the amount of the target cell death determined in a second control sample, wherein the target cells are incubated in the absence of the CAR-expressing immune cells.

In some embodiments, the method further comprises comparing the amount of the target cell death determined in step (c) to the amount of the target cell death determined in a third control sample, wherein the target cells are incubated in the absence of the CAR-expressing immune cells but in the presence of a detergent causing target cell death. In certain embodiments, the detergent is Triton X-100.

In various embodiments, the target cells produce a detectable reporter signal upon said target cells death, and step (c) comprises determining the reporter signal in the test sample, step (d) comprises determining the reporter signal in the first control sample, and step (e) comprises comparing the reporter signals determined in steps (c) and (d).

In some embodiments, the reporter signal is luminescence. In some embodiments, the reporter signal is fluorescence. In some embodiments, the target cells express a reporter protein that produces a signal when the target cell undergoes cell death. In some embodiments, the reporter protein is beta-galactosidase, luciferase, or Green Fluorescent Protein (GFP), or a variant or derivative thereof. In some embodiments, the inhibitory molecule specifically binds to the antigen on the target cells which antigen interacts with the CAR.

In some embodiments, the inhibitory molecule specifically binds to the CAR. In some embodiments, the inhibitory molecule specifically binds to a region within the CAR that specifically binds to the antigen expressed on the target cells. In some embodiments, the inhibitory molecule is an antibody or antibody fragment. In certain embodiments, the antibody is an anti-idiotype antibody. In some embodiments, the antibody fragment is Fab, Fab', $F(ab')_2$, a Fv or Fd fragment, a single chain antibody (scFv), a linear antibody, a single domain antibody, a heavy chain variable region (VH) domain, or a light chain variable region (VL) domain. In some embodiments, the antibody or antibody fragment specifically binds to an antigen within the scFv domain of the CAR. In some embodiments, the antibody or antibody fragment specifically binds to a CDR within the scFv domain of the CAR. In some embodiments, the antibody or antibody fragment specifically binds to an antigen within the VH domain or the VL domain of the CAR. In some embodiments, the antibody or antibody fragment specifically binds to a CDR within the VH domain or the VL domain of the CAR. In some embodiments, the inhibitory molecule is a soluble form of the antigen expressed on the target cells that interacts with the CAR, or a functional fragment or a derivative thereof.

In some embodiments, the immune cells are selected from T cells, induced pluripotent stem cells (iPSC) and natural killer (NK) cells. In some embodiments, the CAR interacts with a B-Cell maturation Antigen (BCMA) receptor, the target cells comprise the BCMA receptor and the inhibitory molecule is a soluble extracellular domain of BCMA. In some embodiments, the target cells are multiple myeloma cells. In certain embodiments, the multiple myeloma cells are MM-1R cells.

In some embodiments, the CAR interacts with a G protein-coupled receptor, class C group 5 member D (GPRC5D), the target cells comprise the GPRC5D receptor and the inhibitory molecule is an anti-idiotype antibody or antibody fragment to the CAR. In some embodiments, the CAR interacts with a G protein-coupled receptor, class C group 5 member D (GPRC5D), the target cells comprise the GPRC5D receptor and the inhibitory molecule is an anti-idiotype antibody or antibody fragment to the GPRC5D receptor. In some embodiments, the target cells are multiple myeloma cells. In certain embodiments, the multiple myeloma cells are MM-1R cells.

In some embodiments, the CAR interacts with kallikerin 2 (KLK2), the target cells comprise the KLK2 and the inhibitory molecule is a soluble KLK2 protein. In some embodiments, the target cells are prostate cells. In some embodiments, the prostate cancer cells are LNCaP cells.

In various embodiments, the method is conducted in a high throughput format.

BRIEF DESCRIPTION OF THE DRAWINGS

FIG. 1A illustrates flow cytometry results that demonstrate BCMA-specific competition of labeled BCMA protein on the surface of LCAR-B38M CAR-T cells. Sample 1 is labeled FITC-BCMA only.

FIG. 1B illustrates flow cytometry results that demonstrate BCMA-specific competition of labeled BCMA protein on the surface of LCAR-B38M CAR-T cells. Sample 6s is FITC-BCMA competition with un-labeled BCMA.

DETAILED DESCRIPTION

The disclosed methods may be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods.

All patents published patent applications and publications cited herein are incorporated by reference as if set forth fully herein.

When a list is presented, unless stated otherwise, it is to be understood that each individual element of that list, and every combination of that list, is a separate embodiment. For example, a list of embodiments presented as “A, B, or C” is to be interpreted as including the embodiments, “A,” “B,” “C,” “A or B,” “A or C,” “B or C,” or “A, B, or C.”

Definitions

As used herein the specification, “a” or “an” may mean one or more. As used herein in the claim(s), when used in conjunction with the word “comprising”, the words “a” or “an” may mean one or more than one.

The use of the term “or” in the claims is used to mean “and/or” unless explicitly indicated to refer to alternatives only or the alternatives are mutually exclusive, although the disclosure supports a definition that refers to only alternatives and “and/or.” As used herein “another” may mean at least a second or more.

“About” means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, “about” means within a range of from 10% below the value to 10% above the value, e.g. from 90 to 110 if the value is 100.

As used herein the terms “encode” or “encoding” with reference to a nucleic acid are used to make the invention readily understandable by the skilled artisan; however, these terms may be used interchangeably with “comprise” or “comprising,” respectively.

“Antigen” refers to any molecule (e.g., protein, peptide, polysaccharide, glycoprotein, glycolipid, nucleic acid, portions thereof, or combinations thereof) capable of being bound by an antigen binding domain or a T-cell receptor that is capable of mediating an immune response. Exemplary immune responses include antibody production and activation of immune cells, such as T cells, B cells or NK cells. Antigens may be expressed by genes, synthesized, or purified from biological samples such as a tissue sample, a tumor sample, a cell or a fluid with other biological components, organisms, subunits of proteins/antigens, killed or inactivated whole cells or lysates.

“Antibodies” is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (κ) and lambda (λ), based on the amino acid sequences of their constant domains.

The term "antibody fragment" refers to at least one portion of an intact antibody, or recombinant variants thereof, that retains the antigen binding properties of the parental full length antibody. It refers to, for example, the antigen binding domain, e.g., an antigenic determining variable region of an intact antibody, that is sufficient to confer recognition and binding, e.g., specific binding of the antibody fragment to a target, such as an antigen. "Antigen-binding fragment" refers to a portion of an immunoglobulin molecule. Examples of antibody fragments include, but are not limited to, Fab, Fab', $F(ab')_2$, and Fv fragments, single chain antibodies (scFv), linear antibodies, single domain antibodies such as sdAb (either VL or VH), camelid VHH domains, and multi-specific antibodies formed from antibody fragments.

The term "subject" is intended to include living organisms in which an immune response can be elicited (e.g., mammals, e.g., humans). Examples of subjects include humans, monkeys, chimpanzees, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors.

"Chimeric antigen receptor" (CAR) as used herein is defined as a cell-surface receptor comprising an extracellular target-binding domain, a transmembrane domain and an intracellular signaling domain, all in a combination that is not naturally found together on a single protein. This includes receptors wherein the extracellular domain and the intracellular signaling domain are not naturally found together on a single receptor protein. CARs are intended primarily for use with lymphocyte such as T cells and natural killer (NK) cells.

"Complementarity determining regions" (CDR) are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) J Exp Med 132:211-50; Kabat et al., Sequences of Proteins of Immunological Interest, 5th Ed. Public Health Service, National Institutes of Health, Bethesda, Md., 1991), Chothia (Chothia et al. (1987) J Mol Biol 196:901-17), IMGT (Lefranc et al. (2003) Dev Comp Immunol 27:55-77) and AbM (Martin and Thornton J Bmol Biol 263:800-15, 1996). The correspondence between the various delineations and variable region numbering is described (see e.g. Lefranc et al. (2003) Dev Comp Immunol 27:55-77; Honegger and Pluckthun, J Mol Biol (2001) 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

The terms "decrease" and "reduce" are used interchangeably herein, and refers generally to the ability of a test molecule to mediate a reduced response (i.e., downstream effect) when compared to the response mediated by a control or a vehicle. Exemplary responses are T cell expansion, T cell activation or T-cell mediated tumor cell killing or binding of a protein to its antigen or receptor, enhanced binding to a Fcγ or enhanced Fc effector functions such as enhanced ADCC, CDC and/or ADCP. Decrease may be a statistically significant difference in the measured response between the test molecule and the control (or the vehicle), or a decrease in the measured response, such as a decrease of about 1.1, 1.2, 1.5, 2, 3, 4, 5, 6, 7, 8, 9, 10, 15, 20 or 30 fold or more, such as 500, 600, 700, 800, 900 or 1000 fold or more (including all integers and decimal points in between and above 1, e.g., 1.5, 1.6, 1.7. 1.8, etc.).

The terms "enhance," "promote," "increase," "expand" or "improve" refer generally to the ability of a test molecule to mediate a greater response (i.e., downstream effect) when compared to the response mediated by a control or a vehicle. Exemplary responses are T cell expansion, T cell activation or T-cell mediated tumor cell killing or binding of a protein to its antigen or receptor, enhanced binding to a Fcγ or enhanced Fc effector functions such as enhanced ADCC, CDC and/or ADCP. Enhance may be a statistically significant difference in the measured response between the test molecule and control (or vehicle), or an increase in the measured response, such as an increase of about 1.1, 1.2, 1.5, 2, 3, 4, 5, 6, 7, 8, 9, 10, 15, 20 or 30 fold or more, such as 500, 600, 700, 800, 900 or 1000 fold or more (including all integers and decimal points in between and above 1, e.g., 1.5, 1.6, 1.7. 1.8, etc.).

"dAb" or "dAb fragment" refers to an antibody fragment composed of a VH domain (Ward et al., Nature 341:544 546 (1989)).

"Fab" or "Fab fragment" refers to an antibody fragment composed of VH, CH1, VL and CL domains.

"$F(ab')_2$" or "$F(ab')_2$ fragment" refers to an antibody fragment containing two Fab fragments connected by a disulfide bridge in the hinge region.

"Fd" or "Fd fragment" refers to an antibody fragment composed of VH and CH1 domains.

"Fv" or "Fv fragment" refers to an antibody fragment composed of the VH and the VL domains from a single arm of the antibody.

"Full length antibody" is comprised of two heavy chains (HC) and two light chains (LC) inter-connected by disulfide bonds as well as multimers thereof (e.g. IgM). Each heavy chain is comprised of a heavy chain variable domain (VH) and a heavy chain constant domain, the heavy chain constant domain comprised of subdomains CH1, hinge, CH2 and CH3. Each light chain is comprised of a light chain variable domain (VL) and a light chain constant domain (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Humanized antibody" refers to an antibody in which at least one CDR is derived from non-human species and at least one framework is derived from human immunoglobulin sequences. A humanized antibody may include substitutions in the frameworks so that the frameworks may not be exact copies of expressed human immunoglobulin or human immunoglobulin germline gene sequences.

"Intracellular signaling domain" or "cytoplasmic signaling domain" refers to an intracellular portion of a molecule. It is the functional portion of the protein which acts by transmitting information within the cell to regulate cellular activity via defined signaling pathways by generating second messengers or functioning as effectors by responding to such messengers. The intracellular signaling domain generates a signal that promotes an immune effector function of the CAR containing cell, e.g., a CAR-T cell.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Natural killer cell" and "NK cell" are used interchangeably and synonymously herein. NK cell refers to a differentiated lymphocyte with a $CD16^+$ $CD56^+$ and/or $CD57^+$ $TCR^-$ phenotype. NK cells are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"Protein" or "polypeptide" are used interchangeably herein are refers to a molecule that comprises one or more polypeptides each comprised of at least two amino acid residues linked by a peptide bond. Protein may be a monomer, or may be protein complex of two or more subunits, the subunits being identical or distinct. Small polypeptides of less than 50 amino acids may be referred to as "peptides". Protein may be a heterologous fusion protein, a glycoprotein, or a protein modified by post-translational modifications such as phosphorylation, acetylation, myristoylation, palmitoylation, glycosylation, oxidation, formylation, amidation, citrullination, polyglutamylation, ADP-ribosylation, PEGylation or biotinylation. Protein may be recombinantly expressed.

"Recombinant" refers to polynucleotides, polypeptides, vectors, viruses and other macromolecules that are prepared, expressed, created or isolated by recombinant means. The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and known in the art.

"Single chain Fv" or "scFv" refers to a fusion protein comprising at least one antibody fragment comprising a light chain variable region (VL) and at least one antibody fragment comprising a heavy chain variable region (VH), wherein the VL and the VH are contiguously linked via a polypeptide linker, and capable of being expressed as a single chain polypeptide. Unless specified, as used herein, a scFv may have the VL and VH variable regions in either order, e.g., with respect to the N-terminal and C-terminal ends of the polypeptide, the scFv may comprise VL-linker-VH or may comprise VH-linker-VL.

"Specifically binds," "specific binding," "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant ($K_D$) of about $1\times10^{-7}$ M or less, for example about $5\times10^{-8}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein).

"T cell," "T-cell" and "T lymphocyte" are interchangeable and used synonymously herein. "T cell" includes thymocytes, naïve T lymphocytes, memory T cells, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), a tumor infiltrating cytotoxic T cell (TIL; $CD8^+$ T cell), $CD4^+$ $CD8^+$ T cell, or any other subset of T cells. Also included are "NKT cells", which refer to a specialized population of T cells that express a semi-invariant αβ T-cell receptor, but also express a variety of molecular markers that are typically associated with NK cells, such as NK1.1. NKT cells include $NK1.1^+$ and $NK1.1^-$, as well as $CD4^+$, $CD4^-$, $CD8^+$ and $CD8^-$ cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α-and-TCR chains, the TCR in γδ T cells is made up of a γ-chain and a δ-chain. γδ T cells can play a role in immunosurveillance and immunoregulation, and were found to be an important source of IL-17 and to induce robust $CD8^+$ cytotoxic T cell response. Also included are "regulatory T cells" or "Tregs" which refer to T cells that suppress an abnormal or excessive immune response and play a role in immune tolerance. Tregs are typically transcription factor Foxp3-positive $CD4^+$ T cells and can also include transcription factor Foxp3-negative regulatory T cells that are IL-10-producing $CD4^+$T cells.

"Tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

"Variant," "mutant" or "altered" refers to a polypeptide or a polynucleotide that differs from a reference polypeptide or a reference polynucleotide by one or more modifications, for example one or more substitutions, insertions or deletions.

The "potency" of a cell (e.g., a CAR-T cell), as referred to herein, is an indicator or measure of its efficacy or potential efficacy in achieving a desired function. In the case of a CAR-T cell, a desired function can be targeting or killing another cell, such as a target cell (e.g., tumor cell). Potency can be assessed directly, by determination of the effect of the cell on its target (e.g., the effect of a CAR-T cell on a tumor cell in vitro or in vivo). Alternatively, potency can be measured indirectly, as in various methods of the present invention. In particular, potency of a CAR-T cell can be assessed by determining the level of in vitro, antigen-specific cytotoxicity of the cell in an assay, e.g., as described herein (relative to, e.g., the cytotoxicity of an unstimulated CAR-T cell as described herein). This measure of potency can then be correlated with, and thus can be considered predictive of, in vivo properties of the cell, such as PK/PD parameters as described herein (e.g., CMAX, T AX, and AUC), which can relate to the effectiveness of the cell in killing its targets. As described further herein, potency can be expressed in terms of a cytotoxicity index, which can be normalized based on the number of cells expressing a relevant CAR.

As used herein, "reference" or "control" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing—cytoplasmic signaling sequences include, but are not limited to, those derived from CD3 zeta, common FcR gamma (FCER1 G), Fc gamma Rlla, FcR beta (Fc Epsilon R1 b), CD3 gamma, CD3 delta, CD3 epsilon, CD79a, CD79b, DAP1 0, and DAP12. In the CAR, the intracellular signaling domain may comprise an intracellular signaling sequence, e.g., a primary signaling sequence of CD3-zeta.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Chimeric Antigen Receptors

Immune cells (e.g., T-cells) may be genetically modified to stably express a desired chimeric antigen receptor. A chimeric antigen receptor (CAR) is an artificially constructed hybrid protein or polypeptide containing the antigen binding domains of an antibody (scFv) linked to immune cell, e.g., T-cell, signaling domains. Characteristics of CARs can include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigens independent of antigen processing, thus bypassing a major mechanism of tumor evasion. Moreover, when expressed in T-cells, CARs advantageously do not dimerize with endogenous T cell receptor (TCR) alpha and beta chains.

The CARs described herein provide recombinant polypeptide constructs comprising at least an extracellular antigen binding domain, a transmembrane domain and an intracellular signaling domain (also referred to herein as "a cytoplasmic signaling domain") comprising a functional signaling domain derived from a stimulatory molecule as defined below. T cells expressing a CAR are referred to herein as CAR T cells, CAR-T cells or CAR modified T cells, and these terms are used interchangeably herein. The cell can be genetically modified to stably express an antibody binding domain on its surface, conferring novel antigen specificity that is MHC independent.

In some instances, the T cell is genetically modified to stably express a CAR that combines an antigen recognition domain of a specific antibody with an intracellular domain of the CD3-zeta chain or FcγRI protein into a single chimeric protein. In one embodiment, the stimulatory molecule is the zeta chain associated with the T cell receptor complex.

An "intracellular signaling domain," or a "cytoplasmic signaling domain", as used herein, refers to an intracellular portion of a molecule. It is the functional portion of the protein which acts by transmitting information within the cell to regulate cellular activity via defined signaling pathways by generating second messengers or functioning as effectors by responding to such messengers. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a co-stimulatory intracellular domain. Example co-stimulatory intracellular signaling domains include those derived from molecules responsible for co-stimulatory signals, or antigen independent stimulation. For example, in the case of a CAR-T, a primary intracellular signaling domain can comprise a cytoplasmic sequence of a T cell receptor, and a co-stimulatory intracellular signaling domain can comprise cytoplasmic sequence from co-receptor or co-stimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3-zeta, FcR gamma, FcR beta, CD3 gamma, CD3 delta, CD3 epsilon, CD5, CD22, CD79a, CD79b, and CD66d DAP10 and DAP12.

The term "zeta" or alternatively "zeta chain", "CD3-zeta" or "TCR-zeta" is defined as the protein provided as GenBank Acc. No. BAG36664.1, or the equivalent residues from a nonhuman species, e.g., murine, rabbit, primate, mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain that are sufficient to functionally transmit an initial signal necessary for T cell activation. In one aspect, the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO: 10 below, or a sequence having at least 50, at least 55, at least 60, at least 65, at least 70, at least 75, at least 80, at least 85, at least 90, at least 95, at least 98 or at least 99%, sequence identity with SEQ ID NO: 10.

```
                                              (SEQ ID NO: 10)
RVKFSRSADAPAYKQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR
```

The term "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules are cell surface molecules other than antigen receptors or their ligands that are required for an efficient immune response. Co-stimulatory molecules include but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137).

A co-stimulatory intracellular signaling domain can be the intracellular portion of a co-stimulatory molecule. A co-stimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, MyD88, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

The term "4-1BB" or alternatively "CD137" refers to a member of the TNFR superfamily with an amino acid sequence provided as GenBank Acc. No. AAA62478.2, or the equivalent residues from a nonhuman species, e.g., mouse, rodent, monkey, ape and the like; and a "4-1BB co-stimulatory domain" is defined as amino acid residues 214-255 of GenBank accession no. AAA62478.2, or the equivalent residues from a non-human species, e.g., mouse, rodent, monkey, ape and the like. In one aspect, the "4-1BB co-stimulatory domain" or "CD137 co-stimulatory domain" is the sequence provided as SEQ ID NO: 11 below or the equivalent residues from a non-human species, e.g., mouse, rodent, monkey, ape and the like, or a sequence having at least 50, at least 55, at least 60, at least 65, at least 70, at least 75, at least 80, at least 85, at least 90, at least 95, at least 98 or at least 99%, sequence identity with SEQ ID NO: 11.

KRGRKKLLY-
IFKQPFMRPVQTTQEEDGCSCRFPEEEEGGCEL
(SEQ ID NO: 11)

In one embodiment, a transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one example embodiment, the transmembrane domain comprises the CD8a hinge domain.

In some embodiments, the cytoplasmic signaling domain further comprises one or more functional signaling domains derived from at least one co-stimulatory molecule as defined herein. In one embodiment, the co-stimulatory molecule is chosen from 4-1BB (i.e., CD137), CD27, CD3-zeta and/or CD28, CD28 is a T cell marker important in T cell co-stimulation. CD27 is a member of the tumor necrosis factor receptor superfamily and acts as a co-stimulatory immune checkpoint molecule. 4-1BB transmits a potent co-stimulatory signal to T cells, promoting differentiation and enhancing long-term survival of T lymphocytes. CD3-zeta associates with TCRs to produce a signal and contains immunoreceptor tyrosine-based activation motifs (ITAMs). In another embodiment, the co-stimulatory molecule is MyD88 or CD40.

In one embodiment, the CAR comprises an intracellular hinge domain comprising CD8 and an intracellular T cell receptor signaling domain comprising CD28, 4-1BB, and CD3-zeta. In another embodiment, the CAR comprises an intracellular hinge domain and an intracellular T cell receptor signaling domain comprising CD28, 4-1BB, and CD3-zeta, wherein the hinge domain comprises all or part of the extracellular region of CD8, CD4 or CD28; all or part of an antibody constant region; all or part of the FcγRIIIa receptor, an IgG hinge, an IgM hinge, an IgA hinge, an IgD hinge, an IgE hinge, or an Ig hinge. The IgG hinge may be from IgG1, IgG2, IgG3, IgG4, IgM1, IgM2, IgA1, IgA2, IgD, IgE, or a chimera thereof.

CARs described herein provide recombinant polypeptide constructs comprising at least an extracellular antigen binding domain, a transmembrane domain and an intracellular signaling domain (also referred to herein as "a cytoplasmic signaling domain") comprising, e.g., a functional signaling domain derived from a stimulatory molecule as defined below. In one embodiment, the CAR comprises a chimeric fusion protein comprising an extracellular antigen recognition domain, a transmembrane domain and an intracellular signaling domain comprising a functional signaling domain derived from a stimulatory molecule. In one embodiment, the CAR comprises a chimeric fusion protein comprising an extracellular antigen recognition domain, a transmembrane domain and an intracellular signaling domain comprising a functional signaling domain derived from a co-stimulatory molecule and a functional signaling domain derived from a stimulatory molecule. In one embodiment, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule.

CARs can be designed to comprise the CD28 and/or 4-1BB signaling domain by itself or be combined with any other desired cytoplasmic domain(s) useful in the context of the CARs described herein. In one embodiment, the cytoplasmic domain of the CAR can further comprise the signaling domain of CD3-zeta. For example, the cytoplasmic domain of the CAR can include but is not limited to CD3-zeta, 4-1BB and CD28 signaling modules and combinations thereof.

In some embodiments, the CARs described herein comprise an extracellular antigen binding domain that specifically binds a tumor antigen. Non-limiting examples of tumor antigens that can be recognized by a CAR described herein include BCMA, GPRC5D, CD79, KLK2, CD19, CD30, CD33, CD123, and FLT3.

The disclosure further provides variants, e.g., functional variants, of the CARs, nucleic acids, polypeptides, and proteins described herein. "Variant" refers to a polypeptide or a polynucleotide that differs from a reference polypeptide or a reference polynucleotide by one or more modifications for example, substitutions, insertions or deletions. The term "functional variant" as used herein refers to a CAR, polypeptide, or protein having substantial or significant sequence identity or similarity to a parent CAR, polypeptide, or protein, which functional variant retains the biological activity of the CAR, polypeptide, or protein for which it is a variant. Functional variants encompass, e.g., those variants of the CAR, polypeptide, or protein described herein (the parent CAR, polypeptide, or protein) that retain the ability to recognize target cells (e.g., tumor cells) to a similar extent, the same extent, or to a higher extent, as the parent CAR, polypeptide, or protein. In reference to the parent CAR, polypeptide, or protein, the functional variant can, for example, be at least about 30%, about 40%, about 50%, about 60%, about 75%, about 80%, about 85%, about 90%, about 91%, about 92%, about 93%, about 94%, about 95%, about 96%, about 97%, about 98%, about 99% or more identical in amino acid sequence to the parent CAR, polypeptide, or protein.

A functional variant can, for example, comprise the amino acid sequence of the parent CAR, polypeptide, or protein with at least one conservative amino acid substitution. In another embodiment, the functional variants can comprise the amino acid sequence of the parent CAR, polypeptide, or protein with at least one non-conservative amino acid substitution. In this case, the non-conservative amino acid substitution may not interfere with or inhibit the biological activity of the functional variant. The non-conservative amino acid substitution may enhance the biological activity of the functional variant such that the biological activity of the functional variant is increased as compared to the parent CAR, polypeptide, or protein.

Amino acid substitutions of the inventive CARs may be conservative amino acid substitutions. Conservative amino acid substitutions are known in the art, and include amino acid substitutions in which one amino acid having certain physical and/or chemical properties is exchanged for another amino acid that has the same or similar chemical or physical properties. For example, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The CAR, polypeptide, or protein can consist essentially of the specified amino acid sequence or sequences described herein, such that other components e.g., other amino acids, do not materially change the biological activity of the functional variant.

The CARs, polypeptides, and proteins of embodiments of the disclosure (including functional portions and functional variants) can be of any length, i.e., can comprise any number of amino acids, provided that the CARs, polypeptides, or proteins (or functional portions or functional variants thereof) retain their biological activity, e.g., the ability to specifically bind to an antigen, detect diseased cells (e.g., cancer cells) in a host, or treat or prevent disease in a host, etc. For example, the polypeptide can be about 50 to about 5000 amino acids long, such as about 50, about 70, about 75, about 100, about 125, about 150, about 175, about 200, about 225, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000 or more amino acids in length. The polypeptides described herein also include oligopeptides.

The CARs, polypeptides, and proteins used in the aspects and embodiments herein (including functional portions and functional variants of the CARs) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, α-(2-amino-2-norbornane)-carboxylic acid, α,γ-diaminobutyric acid, α,β-diaminopropionic acid, homophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, indoline-2-carboxylic acid, 1,2,3,4-tetrahydroisoquinoline-3-carboxylic acid, aminomalonic acid, aminomalonic acid monoamide, and α-tert-butylglycine.

The CARs, polypeptides, and proteins used in the aspects and embodiments herein (including functional portions and functional variants) can be subject to post-translational modifications. They can be glycosylated, esterified, N-acylated, amidated, carboxylated, phosphorylated, esterified, cyclized via, e.g., a disulfide bridge, or converted into an acid addition salt. In some embodiments, they are dimerized or polymerized, or conjugated.

The CARs, polypeptides, and/or proteins used in the aspects and embodiments herein (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; and *Epitope Mapping*, ed. Westwood et al., Oxford University Press, Oxford, United Kingdom, 2001. Also, polypeptides and proteins can be recombinantly produced using the nucleic acids described herein using standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the CARs, polypeptides, and proteins described herein (including functional portions and functional variants thereof) can be isolated and/or purified from a source, such as a plant, a bacterium, an insect, a mammal, etc. Methods of isolation and purification are known in the art. Alternatively, the CARs, polypeptides, and/or proteins described herein (including functional portions and functional variants thereof) can be commercially synthesized. In this respect, the CARs, polypeptides, and proteins can be synthetic, recombinant, isolated, and/or purified.

Examples of modified nucleotides that can be used to generate the recombinant nucleic acids utilized to produce the polypeptides described herein include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, carboxymethylaminomethyl-2-thiouridine, 5-carboxymethylaminomethyluracil, dihydrouracil, $N^6$-substituted adenine, 7-methylguanine, 5-methylaminomethyluracil, 5-methoxyaminomethyl-2-thiouracil, beta-D-mannosylqueosine, 5"-methoxycarboxymethyluracil, 5-methoxyuracil, 2-methylthio-$N^6$-isopentenyladenine, uracil-5-oxyacetic acid (v), wybutoxosine, pseudouracil, queuosine, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

The nucleic acid can comprise any isolated or purified nucleotide sequence which encodes any of the CARs, polypeptides, or proteins, or functional portions or functional variants thereof. Alternatively, the nucleotide sequence can comprise a nucleotide sequence which is degenerate to any of the sequences or a combination of degenerate sequences. The nucleic acids can be incorporated into a recombinant expression vector. Recombinant expression vectors comprising one or more of the nucleic acids may be used. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

The recombinant expression vector can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-Cl, pMAM, and pMAMneo (Clontech). The recombinant expression vector may be a viral vector, e.g., a retroviral vector, e.g., a gamma retroviral vector.

The recombinant expression vectors are prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol×resistance genes, histidinol resistance genes, tetracycline resistance genes, and ampicillin resistance genes.

The recombinant expression vector can comprise a native or normative promoter operably linked to the nucleotide sequence encoding the CAR, polypeptide, or protein (including functional portions and functional variants thereof), or to the nucleotide sequence which is complementary to or which hybridizes to the nucleotide sequence encoding the CAR, polypeptide, or protein. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40 promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

The inhibitory molecule can be an antibody (e.g., monoclonal antibody), or antigen binding portion thereof, or a soluble antigen, or a functional portion or functional variant thereof, which binds, e.g., specifically binds, to an epitope of the CAR of the immune cell. The antibody can be any type of immunoglobulin that is known in the art. Immunoglobulins may be assigned to five major classes, IgA, IgD, IgE, IgG and IgM. IgA and IgG are further classified as the isotypes IgA1, IgA2, IgG1, IgG2, IgG3 and IgG4. Antibody light chains of vertebrate species can be assigned to one of two types, kappa (κ) and lambda (λ), based on the amino acid sequences of their constant domains. The antibody can be of any class or isotype.

The antibodies used in the methods described herein can include immunoglobulin molecules including monoclonal antibodies including murine, human, humanized and chimeric monoclonal antibodies, polyclonal, antigen-binding fragments, bispecific or multispecific antibodies, monomeric, dimeric, tetrameric or multimeric antibodies, single chain antibodies, domain antibodies and any other modified configuration of the immunoglobulin molecule that comprises an antigen binding site of the required specificity. The antibody can be a naturally-occurring antibody, e.g., an antibody isolated and/or purified from a mammal, e.g., a murine, primate, mouse, rabbit, goat, horse, chicken, hamster, human, etc. Alternatively, the antibody can be an engineered (e.g., genetically-engineered) antibody.

Humanized antibodies have antigen binding sites derived from non-human species and the variable region frameworks are derived from human immunoglobulin sequences. Human antibodies have heavy and light chain variable regions in which both the framework and the antigen binding site are derived from sequences of human origin.

Also, the antibody can have any level of affinity or avidity for the functional portion of the CAR. In some embodiments, the antibody may bind the hK2 antigen with a range of affinities ($K_D$). In various embodiments, the antibody binds to the hK2 antigen with high affinity, for example, with a $K_D$ equal to or less than about $10^{-7}$ M, such as but not limited to, 1-9.9 (or any range or value therein, such as 1, 2, 3, 4, 5, 6, 7, 8, or 9)$\times 10^{-8}$M, $10^{-9}$ M, $10^{-10}$ M, $10^{-11}$ M, $10^{-12}$ M, $10^{-13}$ M, $10^{-14}$ M, $10^{-15}$ M or any range or value therein, as determined by surface plasmon resonance or the Kinexa method, as practiced by those of skill in the art. One example affinity is equal to or less than $1\times 10^{-8}$ M. Another example affinity is equal to or less than $1\times 10^{-9}$ M.

Methods of testing antibodies for the ability to bind to any functional portion of the CARs are known in the art and include any antibody-antigen binding assay, such as, for example, radioimmunoassay (RIA), Western blot, enzyme-linked immunosorbent assay (ELISA), immunoprecipitation, and competitive inhibition assays.

Suitable methods of making antibodies are known in the art. For instance, standard hybridoma methods are described in, e.g., Köhler and Milstein, *Eur. J. Immunol.,* 5, 511-519 (1976), Harlow and Lane (eds.), *Antibodies: A Laboratory Manual*, CSH Press (1988), and C. A. Janeway et al. (eds.), *Immunobiology,* 5th Ed., Garland Publishing, New York, N.Y. (2001)). Alternatively, other methods, such as EBV-hybridoma methods (Haskard and Archer, *J. Immunol. Methods,* 74(2), 361-67 (1984), and Roder et al., *Methods Enzymol.,* 121, 140-67 (1986)), and bacteriophage vector expression systems (see, e.g., Huse et al., *Science,* 246, 127581 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display can also be used to generate an antibody used in any of the methods described herein. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen (i.e., hK2), and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are known in the art and are described in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994). Antibodies, as utilized herein, can be multiple or single chain, or intact immunoglobulins, and may be derived from natural sources or from recombinant sources. Antibodies can be tetramers of immunoglobulin molecules.

Also provided are antigen binding portions of any of the antibodies described herein. The antigen binding portion can be any portion that has at least one antigen binding site, such as Fab, F(ab')$_2$, dsFv, sFv, diabodies, and triabodies. In some embodiments, antigen-binding fragments are heavy chain complementarity determining regions (HCDR) 1, 2 and/or 3, light chain complementarity determining regions (LCDR) 1, 2 and/or 3, a heavy chain variable region (VH), or a light chain variable region (VL), Fab, F(ab')$_2$, Fd and Fv fragments and domain antibodies (dAb) comprising (e.g., consisting of) either one VH domain or one VL domain. VH and VL domains may be linked together via a linker, e.g., a synthetic linker.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Also provided by the present disclosure is a nucleic acid comprising a nucleotide sequence encoding any of the CARs, polypeptides, or proteins described herein (including functional portions and functional variants thereof).

The portion of the CAR comprising an antibody or antibody fragment thereof may exist in a variety of forms where the antigen binding domain is expressed as part of a contiguous polypeptide chain including, for example, a single domain antibody fragment (sdAb), a scFv and a human chimeric or humanized antibody (Harlow et al., 1999, *In: Using Antibodies: A Laboratory Manual*, Cold Spring Harbor Laboratory Press, N.Y.; Harlow et al., 1989, *In: Antibodies: A Laboratory Manual*, Cold Spring Harbor, N.Y.; Houston et al., 1988, *Proc. Natl. Acad. Sci. USA* 85:5879-5883; Bird et al., 1988, *Science* 242:423-426). In one aspect, the antigen binding domain of the CAR composition comprises an antibody fragment. In one aspect, the CAR comprises an antibody fragment that comprises a scFv.

In one embodiment, the extracellular antigen-binding domain comprises a scFv. In some embodiments, the scFv comprises a linker polypeptide between the light chain variable region and the heavy chain variable region.

In recombinant expression systems, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to hK2.

The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

In one embodiment, the extracellular antigen-binding domain comprises a signal polypeptide. The signal polypeptide may be positioned at the N-terminus of the extracellular antigen binding domain that binds hK2. The signal polypeptide may be optionally cleaved from the extracellular antigen binding domain during cellular processing and localization of the CAR to the cellular membrane. Any of various signal polypeptides known to one of skill in the art may be used as the signal polypeptide. Non-limiting examples of peptides from which the signal polypeptides may be derived include FcεR, human immunoglobulin (IgG) heavy chain (HC) variable region, CD8a, or any of various other proteins secreted by T cells. In various embodiments, the signal polypeptide is compatible with the secretory pathway of a T cell.

In one aspect, the disclosure provides a CAR comprising an extracellular antigen-binding domain, a transmembrane domain and an intracellular signaling domain. In one embodiment, the intracellular signaling domain comprises a polypeptide component selected from the group consisting of a TNF receptor superfamily member 9 (CD137) component, a T-cell surface glycoprotein CD3 zeta chain (CD3z) component, a cluster of differentiation (CD27) component, a cluster of differentiation superfamily member (such as, e.g., CD28 or inducible T-cell co-stimulator (ICOS)) component, and a combination thereof. In one embodiment, the transmembrane domain comprises a CD8a transmembrane region (CD8a-TM) polypeptide. In one embodiment, the transmembrane domain comprises at least the transmembrane region(s) of) the α, β or ζ chain of the T-cell receptor, CD28, CD3 epsilon, CD45, CD4, CD5, CD8, CD8a, CD9, CD16, CD22, CD33, CD37, CD40, CD64, CD80, CD86, CD134, CD137, CD154. In another embodiment, the transmembrane domain comprises at least the transmembrane domain of ζ, η or FcεR1γ and -β, MB1 (Igα), B29 or CD3-γ, ζ, or η. In another embodiment, the transmembrane domain is synthetic, e.g., comprising predominantly hydrophobic residues such as leucine and valine, a triplet of phenylalanine, or tryptophan.

In one embodiment, the CAR further comprises a hinge region linking the transmembrane domain to the extracellular antigen-binding domain. In some embodiments, the hinge region is a CD8a-hinge region.

In one aspect, the present disclosure provides isolated immunoresponsive cells comprising the CARs described herein. In some embodiments, the isolated immunoresponsive cell is transduced with the CAR, for example, the CAR is constitutively expressed on the surface of the immunoresponsive cell. In certain embodiments, the isolated immunoresponsive cell is further transduced with at least one co-stimulatory ligand such that the immunoresponsive cell expresses the at least one co-stimulatory ligand. In certain embodiments, the at least one co-stimulatory ligand is selected from the group consisting of 4-1BBL, CD48, CD70, CD80, CD86, OX40L, TNFRSF14, and combinations thereof. In certain embodiments, the isolated immunoresponsive cell is further transduced with at least one cytokine such that the immunoresponsive cell secretes the at least one cytokine. In certain embodiments, the at least cytokine is selected from the group consisting of IL-2, IL-3, IL-6, IL-7, IL-11, IL-12, IL-15, IL-17, IL-21, and combinations thereof. In some embodiments, the isolated immunoresponsive cell is selected from the group consisting of a T lymphocyte (T cell), a Natural Killer (NK) cell, a cytotoxic T lymphocyte (CTL), a regulatory T cell, a human embryonic stem cell, a lymphoid progenitor cell, a T cell-precursor cell, and a pluripotent stem cell from which lymphoid cells may be differentiated.

In one embodiment, the CAR T-expressing immune cells of the disclosure can be generated by introducing a lentiviral vector comprising a desired CAR, for example, a CAR comprising anti-hK2, CD8a hinge and transmembrane domain, and human 4-1BB and CD3-zeta signaling domains, into the cells. The CAR T-expressing immune cells of the invention are able to replicate in vivo resulting in long-term persistence that can lead to sustained tumor control.

Any of the CARs and inhibitory molecules can be expressed in host cells comprising any of the recombinant expression vectors described herein. As used herein, the term "host cell" refers to any type of cell that can contain the recombinant expression vector. The host cell can be a eukaryotic cell, e.g., plant, animal, or algae, fungi, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, polypeptide, or protein, the host cell may be a mammalian cell. The host cell may be a human cell. While the host cell can be of any cell type, can originate from any type of tissue, and can be of any developmental stage, the host cell may be a peripheral blood lymphocyte (PBL). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to bone marrow, blood, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD8^+$ T cells (e.g., cytotoxic T cells), $CD4^+$ helper T cells, e.g., $Th_1$ and $Th_2$ cells, peripheral blood mononuclear cells (PBMCs), peripheral blood leukocytes (PBLs), tumor infiltrating cells, memory T cells, naïve T cells, and the like. The T cell may be a $CD8^+$ T cell or a $CD4^+$ T cell.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, an erythrocyte, a neutrophil, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment, the population of cells is a clonal population comprising host cells comprising a recombinant expression vector as described herein.

Inhibitors that Bind to CAR

In some embodiments, the inhibitory molecules used in the methods described herein can be monoclonal antibodies that specifically bind to a CAR polypeptide. For example, the monoclonal antibody can specifically bind to a constant domain of a CAR polypeptide described herein, such as a CAR polypeptide expressed on a CAR-T cell. Alternatively, the antibody can bind to the antigen recognition domain of a CAR polypeptide (e.g., a CD-19-binding CAR polypeptide). The antibody can interfere with the ability of the CAR-T cell to bind to a target cell (e.g., tumor cell). Without wishing to be bound by theory, the antibody can prevent the CAR-T cell from binding to the target cell (e.g., tumor cell).

In various embodiments a monoclonal antibody that binds specifically to a BCMA-targeted CAR polypeptide is used. In some aspects, the monoclonal antibody binds to a BCMA-specific CAR polypeptide and competes for binding of the polypeptide with a multiple myeloma target cell, or any other cell expressing BCMA. The monoclonal antibody can be an anti-idiotype antibody. Anti-idiotype antibodies are specific antibodies that can bind to the CDR sequences within a specific antibody. The monoclonal antibody may be a Type 1 anti-idiotype antibody that binds to the CDRs of a target antibody variable domain in such a manner as to inhibit, disrupt or neutralize the activity of the target antibody, i.e., its ability to bind antigen.

The inhibitory molecule can be an anti-idiotype peptide. In some embodiments, the anti-idiotype peptide binds an antigen binding receptor of one or more additional cellular therapeutics (e.g., an scFv of a CAR-T cell). In some embodiments, the anti-idiotype peptide binds an antigen binding receptor of one or more CDRs of an antigen binding receptor (e.g., an scFv of a CAR-T cell). In various embodiments, the an anti-idiotype antibody or peptide (e.g., scFv) binds to a B-cell specific marker antigen binding portion (e.g., a CAR that binds CD19, CD20, CD21, CD22, CD24, CD79a, CD79b, ROR1, or BCMA) of a CAR-T cell. Additionally, for example, in some embodiments, the anti-idiotype antibody or fragment (e.g., scFv) binds an anti-CD19 antibody or fragment (e.g., an anti-CD19 antibody (e.g., anti-CD19 scFv) expressed by a CAR-T cell).

Also provided are inhibitory molecules that comprise all or part of the heavy chain variable region of a monoclonal antibody that binds specifically to a BCMA-targeted CAR polypeptide. Such inhibitory molecules can also bind specifically to the BCMA-targeted CAR polypeptide. Also provided are inhibitory molecules that comprise all or part of the light chain variable region of a monoclonal antibody that binds specifically to a BCMA-targeted CAR polypeptide. Such inhibitory molecules can also bind specifically to the BCMA-targeted CAR polypeptide. Also provided are inhibitory molecules that comprise one, two, three, four, five, or six complementarity determining region (CDR) from the light variable and/or heavy variable chain of the monoclonal antibody binds to a BCMA-specific CAR polypeptide.

In certain embodiments, a monoclonal antibody that binds specifically to a GPRC5D-targeted CAR polypeptide is used. In some aspects, the monoclonal antibody binds to a GPRC5D-specific CAR polypeptide and competes for binding of the polypeptide with a multiple myeloma target cell (e.g., multiple myeloma tumor cell), or any other cell expressing GPRC5D. The monoclonal antibody can be an anti-idiotype antibody. Also provided are inhibitory molecules that comprise all or part of the heavy chain variable region of a monoclonal antibody that binds specifically to a GPRC5D-targeted CAR polypeptide. Such inhibitory molecules can also bind specifically to the GPRC5D-targeted CAR polypeptide. Also provided are inhibitory molecules that comprise all or part of the light chain variable region of a monoclonal antibody that binds specifically to a GPRC5D-targeted CAR polypeptide. Such inhibitory molecules can also bind specifically to the GPRC5D-targeted CAR polypeptide. Also provided are inhibitory molecules that comprise one, two, three, four, five, or six complementarity determining region (CDR) from the light variable and/or heavy variable chain of the monoclonal antibody binds to a GPRC5D-specific CAR polypeptide.

In certain embodiments, a monoclonal antibody that binds specifically to a CD79-targeted CAR polypeptide is used. In some aspects, the monoclonal antibody binds to a CD79-specific CAR polypeptide and competes for binding of the polypeptide with a multiple myeloma target cell, or any other cell expressing CD79. The monoclonal antibody can be an anti-idiotype antibody. Also provided are inhibitory molecules that comprise all or part of the heavy chain variable region of a monoclonal antibody that binds specifically to a CD79-targeted CAR polypeptide. Such inhibitory molecules can also bind specifically to the CD79-targeted CAR polypeptide. Also provided are inhibitory molecules that comprise all or part of the light chain variable region of a monoclonal antibody that binds specifically to a CD79-targeted CAR polypeptide. Such inhibitory molecules can also bind specifically to the CD79-targeted CAR polypeptide. Also provided are inhibitory molecules that comprise one, two, three, four, five, or six complementarity determining region (CDR) from the light variable and/or heavy variable chain of the monoclonal antibody binds to a CD79-specific CAR polypeptide.

In certain embodiments, a monoclonal antibody that binds specifically to a KLK2-targeted CAR polypeptide is used. In some aspects, the monoclonal antibody binds to a KLK2-specific CAR polypeptide and competes for binding of the polypeptide with a multiple myeloma target cell, or any other cell expressing KLK2. The monoclonal antibody can be an anti-idiotype antibody. Also provided are inhibitory molecules that comprise all or part of the heavy chain variable region of a monoclonal antibody that binds specifically to a KLK2-targeted CAR polypeptide. Such inhibitory molecules can also bind specifically to the KLK2-targeted CAR polypeptide. Also provided are inhibitory molecules that comprise all or part of the light chain variable region of a monoclonal antibody that binds specifically to a KLK2-targeted CAR polypeptide. Such inhibitory molecules can also bind specifically to the KLK2-targeted CAR polypeptide. Also provided are inhibitory molecules that comprise one, two, three, four, five, or six complementarity determining region (CDR) from the light variable and/or heavy variable chain of the monoclonal antibody binds to a KLK2-specific CAR polypeptide. In certain embodiments, a monoclonal antibody that binds specifically to a CD19-targeted CAR polypeptide is used. In some aspects, the monoclonal antibody binds to a CD19-specific CAR polypeptide and competes for binding of the polypeptide with a multiple myeloma target cell, or any other cell expressing CD19. The monoclonal antibody can be an anti-idiotype antibody. Also provided are inhibitory molecules that comprise all or part of the heavy chain variable region of a monoclonal antibody that binds specifically to a CD19-targeted CAR polypeptide. Such inhibitory molecules can also bind specifically to the CD19-targeted CAR polypeptide. Also provided are inhibitory molecules that comprise all or part of the light chain variable region of a monoclonal antibody that binds specifically to a CD19-targeted CAR polypeptide. Such inhibitory molecules can also bind specifically to the CD19-targeted CAR polypeptide. Also provided are inhibitory molecules that comprise one, two, three, four, five, or six complementarity determining region (CDR) from the light variable and/or heavy variable chain of the monoclonal antibody binds to a CD19-specific CAR polypeptide.

In various embodiments, the inhibitory molecule, e.g., monoclonal antibody, fragment of a monoclonal antibody, or derivative of a monoclonal antibody, is capable of transgene-specific expansion. Anti-idiotype antibodies, including antigen-binding fragments thereof, specifically recognizes, is specifically targeted to, and/or specifically binds to an idiotope of an antibody or an antigen binding fragment thereof, e.g., the antigen-binding domain of a recombinant receptor such as a chimeric antigen receptor (CAR). An idiotope is any single antigenic determinant or epitope within the variable portion of an antibody. The anti-idiotype antibodies or antigen-binding fragments thereof can be agonists and/or exhibit specific activity to stimulate cells expressing a particular antibody including conjugates or recombinant receptors containing the same or an antigen-binding fragment thereof (see, e.g., U.S. Pat. Publication Nos. US 2016/0096902; US 2016/0068601; US 2014/0322183; US 2015/0175711; US 2015/283178; U.S. Pat. No. 9,102,760; Jena et al. PloS one (2013) 8(3):e57838; Long et al., Nature Medicine (2015) 21(6): 581-590; Lee et al., The Lancet (2015) 385(9967): 517-528; Zhao et al., PloS One (2014) 9(5):e96697; Leung et al., MAbs. (2015) 7(1):66-76).

In some embodiments, the inhibitory molecule is a soluble form of the antigen expressed on the target cells that interacts with the CAR, or a functional fragment or a derivative thereof. For example, the soluble antigen may be a soluble form of BCMA, GPRC5D, CD79, KLK2, CD19, CD30, CD33, CD123, and FLT3, or a functional fragment or a derivative thereof.

Contacting CAR-T Cell with Inhibitor

Disclosed herein are various methods comprising preventing or modifying the ability of a specific CAR-T cell (e.g., a T cell expressing a BCMA-binding CAR) by contacting the cell with a monoclonal antibody, or soluble antigen, that binds to the antigen recognition domain of the CAR.

In one aspect is provided an in vitro method for determining cytotoxicity of an immune cell expressing a chimeric antigen receptor (CAR) molecule, the method comprising:

a) in a test sample, incubating the CAR-expressing immune cells with target cells (e.g., tumor cells), wherein the target cells express an antigen which interacts with the CAR, b) in a first control sample, incubating the CAR-expressing immune cells with the target cells, wherein said incubation is conducted in the presence of an inhibitory molecule, wherein the inhibitory molecule reduces, inhibits, blocks, and/or prevents interaction between the CAR and the target cells, c) determining the amount of the target cell death in the test sample, d) determining the amount of the target cell death in the first control sample, and e) determining cytotoxicity of CAR-expressing immune cells based on comparing the amount of the target cell death determined in steps (c) and (d), wherein the incubation time, the amount of the CAR-expressing immune cells and the amount of the target cells are substantially the same in the test sample and the first control sample.

In some embodiments, the incubation time of the test sample is 85-115%, 90%-110%, or 95-105% that of the incubation time of the first control sample. In some embodiments, the amount of the CAR-expressing immune cells is 85-115%, 90%-110%, or 95-105% that of the amount of the target cells.

In some embodiments, the incubation steps (a) and (b) are performed simultaneously. Simultaneous performance can allow for some difference between the start time and end time of these steps, e.g., by one hour, 30 minutes, or by 15 minutes. Performing steps (a) and (b) simultaneously can provide for conditions where the incubation time, the amount of the CAR-expressing immune cells and the amount of the target cells are substantially the same. In some embodiments, the determining steps (c) and (d) are performed simultaneously. Simultaneous performance can allow for some difference between the start time and end time of these steps, e.g., by one hour, 30 minutes, or by 15 minutes. Performing steps (c) and (d) simultaneously can provide for conditions where the incubation time, the amount of the CAR-expressing immune cells, and the amount of the target cells are substantially the same.

In some embodiments, the CAR-expressing immune cells and/or the target cells have been pre-incubated with the inhibitory molecule prior to said contacting step.

In some embodiments, the method further comprises comparing the amount of the target cell (e.g., tumor cell) death determined in step (c) to the amount of the target cell death determined in a second control sample, wherein the target cells are incubated in the absence of the CAR-expressing immune cells.

In some embodiments, the method further comprises comparing the amount of the target cell death determined in step (c) to the amount of the target cell death determined in a third control sample, wherein the target cells are incubated in the absence of the CAR-expressing immune cells but in the presence of a detergent causing the target cell death. In certain embodiments, the detergent is Triton X-100.

In various embodiments, the target cells (e.g., tumor cells) produce a detectable reporter signal upon said target cells death, and step (c) comprises determining the reporter signal in the test sample, step (d) comprises determining the reporter signal in the first control sample, and step (e) comprises comparing the reporter signals determined in steps (c) and (d). In some embodiments, the target cells express a reporter protein that produces a signal when the target cell undergoes cell death. Exemplary reporter proteins suitable for use in the methods of the present disclosure include, but are not limited to, beta-galactosidase, luciferase, Green Fluorescent Protein (GFP), Yellow Fluorescent Protein (YFP), Cyan Fluorescent Protein (CFP), Blue Fluorescent Protein (BFP), and variants or derivatives thereof.

In some embodiments, the reporter signal is luminescence. A protein that can generate the reporter signal (e.g., luminescence) may be expressed in a cell compartment. Upon cell death, the protein is released from the cell compartment into media, where the protein can generate a luminescent signal, such as by enzymatically acting upon an agent to generate luminescence. Exemplary cells that can be used in this manner include KILR® target cells. Target cells can be engineered to express an antigen that interacts with the chimeric antigen receptor. In certain embodiments, KILR® MM-1R Multiple Myeloma target cells are used. The target cells can also stably express a protein tagged with a label or enzyme. When the target cell line is used in a cytotoxicity assay, and its membrane is compromised due to cell death, the target cell line can release the tagged protein into the media. The tagged protein can be detected by adding to the media reagents that are substrates of the enzyme tag on the protein. For example, a beta-galactosidase enzyme can hydrolyze the substrate to give a chemiluminescent output. Luminescence can be quantified on a plate reader capable of measuring chemiluminescence. Alternatively, the tagged protein can be detected via assays for detecting the label.

In some embodiments, the reporter signal is fluorescence. A protein that can generate the reporter signal (e.g., fluorescence) may be expressed in a cell compartment. Upon cell death, the protein is released from the cell compartment into media, where the protein can generate a fluorescent signal.

In some embodiments, the inhibitory molecule specifically binds to the antigen on the target cells which interacts with the CAR. Without wishing to be bound by theory, the use of an inhibitory molecule that binds to antigen can provide for a suitable control in a cytotoxicity assay or other related CAR potency assay such that untransfected or mock-transfected immune cells do not need to be used as a control. Such can eliminate the need to produce mock CAR-T cells in parallel to drug product. Production of mock CAR-T cells can impact drug product production in several ways. Eliminating the use of mock cell controls can simplify the manufacturing process, can ensure that patient dosing can be achieved by reducing sampling of any autologous CAR-T cells from the patient, and otherwise reduce cost in CAR-T cell therapy. The methods described herein can also reduce or eliminate testing delays due to mock cell failures. The method can also reduce testing errors through provision of a more simplified format. Reduction of testing delays and errors can also provide for avoidance of production delays and/or patient dosing delays.

In some embodiments, the inhibitory molecule specifically binds to the CAR. In some embodiments, the inhibitory molecule specifically binds to a region within the CAR that specifically binds to the antigen expressed on the target cells that interacts with the CAR. By binding to the CAR, particularly to a region within the CAR that specifically binds to the antigen (e.g., an epitope comprising one or more CDR sequences, or portions thereof), the inhibitory molecule can block the CAR-T cell from interacting with the target cell. Such blocking can prevent the CAR-T cell from killing the target cell. Thus, instead of using a mock transfected immune cell, the patient's own CAR-T cells can be used with addition of the inhibitory molecule as a suitable control instead.

In some embodiments, the inhibitory molecule is an antibody. In certain embodiments, the antibody is an anti-idiotype antibody. The anti-idiotype antibody can compete with the antigen on the host cell for binding to the chimeric antigen receptor. The anti-idiotype antibody can share some structural features with the antigen.

In some embodiments, the antibody or antibody fragment specifically binds to an antigen within the scFv domain of the chimeric antigen receptor. In some embodiments, the antibody or antibody fragment specifically binds to a CDR within the scFv domain. In some embodiments, the antibody or antibody fragment specifically binds to an antigen within the Fab domain of the chimeric antigen receptor. In some embodiments, the antibody or antibody fragment specifically binds to a CDR within the Fab domain. In some embodiments, the antibody or antibody fragment specifically binds to an antigen within the VH or the VL domain of the chimeric antigen receptor. In some embodiments, the antibody or antibody fragment specifically binds to a CDR within the VH or the VL domain.

In some embodiments, the immune cells are selected from T cells, induced pluripotent stem cells (iPSC) and natural killer (NK) cells. In some embodiments, the CAR interacts with a B-Cell maturation Antigen (BCMA) receptor, the target cells comprise the BCMA receptor and the inhibitory molecule is a soluble extracellular domain of BCMA. In some embodiments, the target cells are multiple myeloma cells. In certain embodiments, the multiple myeloma cells are MM-1R cells.

In various other embodiments, the CAR interacts with tumor and disease antigens that include, but are not limited to, BCMA, GPRC5D, CD79, KLK2, CD19, CD30, CD33, CD123, and FLT3.

In some embodiments, the CAR interacts with the tumor antigen GPRC5D. In some embodiments, the GPRC5D receptor is expressed by the target cells. In some embodiments, the inhibitory molecule is an anti-idiotype antibody or antibody fragment to the CAR. In some embodiments, the inhibitory molecule is an anti-idiotype antibody or antibody fragment to the GPRC5D receptor. As a non-limiting example, the target cells are multiple myeloma cells. A non-limiting example of a multiple myeloma cells are MM-1R cells.

In some embodiments, the CAR interacts with the tumor antigen KLK2. In some embodiments, the KLK2 antigen is expressed by target cells. In some embodiments, the inhibitory molecule is a soluble KLK2 protein. As a non-limiting example, the target cells are prostate cancer cells. A non-limiting example of a prostate cells are LNCaP cells.

In various embodiments, the method is conducted in a high throughput format.

Host Cells

The inhibitory molecules described herein may be expressed in a cell, e.g., an immune effector cell, (e.g., a population of cells, e.g., a population of immune effector cells) comprising a nucleic acid molecule, a CAR polypeptide molecule, or a vector as described herein. The immune effector cell may be a T cell or an NK cell, for example. The inhibitory molecules can be expressed in various mammalian cell types (e.g., Chinese hamster ovary cells), and then purified before use in any of the assays described herein.

The CAR-T molecules described herein can be expressed in immune effector cells, e.g., T cells or NK cells. The immune effector cells can be obtained from a unit of blood collected from a subject using any number of techniques known to the skilled artisan, such as Ficoll™ separation. Cells from the circulating blood of an individual can be obtained by apheresis. The apheresis product generally contains lymphocytes, including T cells, monocytes, granulocytes, B cells, other nucleated white blood cells, red blood cells, and platelets. The cells collected by apheresis may be washed to remove the plasma fraction and the cells may then be placed in an appropriate buffer or media for subsequent processing steps. The cells may be washed with phosphate buffered saline (PBS). The wash solution may lack calcium, may lack magnesium, and/or may lack all divalent cations.

The methods described herein can include, e.g., selection of a specific subpopulation of immune effector cells, e.g., T cells, that are a T regulatory cell-depleted population, CD25+ depleted cells, using, e.g., a negative selection technique, e.g., described herein. Preferably, the population of T regulatory depleted cells contains less than 30%, 25%, 20%, 15%, 10%, 5%, 4%, 3%, 2%, 1% of CD25+ cells.

Potency Assays

Disclosed herein are methods for characterizing the potency of chimeric antigen receptor (CAR)-T cells (CAR-T cells). The methods include (a) stimulating a CAR-T cell in an antigen-specific manner (i.e., via the CAR of the CAR-T cell), and (b) determining the level of antigen-specific cytotoxicity of the stimulated cell.

In one aspect is provided an in vitro method for determining potency of an immune cell expressing a chimeric antigen receptor (CAR) molecule, the method comprising:

a) in a test sample, incubating the CAR-expressing immune cells with target cells (e.g., tumor cells), wherein the target cells express an antigen which interacts with the CAR,
b) in a first control sample, incubating the CAR-expressing immune cells with the target cells, wherein said incubation is conducted in the presence of an inhibitory molecule, wherein the inhibitory molecule reduces, inhibits, blocks, and/or prevents interaction between the CAR and the target cells,
c) determining the amount of interaction between the CAR-expressing immune cells and the target cells in the test sample,
d) determining the amount of interaction between the CAR-expressing immune cells and the target cells in the first control sample, and
e) determining potency of CAR-expressing immune cells based on comparing the amount of the interaction determined in steps (c) and (d), wherein the incubation time, the amount of the CAR-expressing immune cells and the amount of the target cells are substantially the same in the test sample and the first control sample.

The interaction between the CAR-expressing immune cells and the target cells can be measured directly, such as by assessing binding of CAR-expressing immune cells and the target cells. The interaction between the CAR-expressing immune cells and the target cells can be measured indirectly, such as by assessing cell death, apoptosis, necrosis, release of cytokines, changes in cell morphology, etc.

In some embodiments, the incubation time of the test sample is 85-115%, 90%-110%, or 95-105% that of the incubation time of the first control sample. In some embodiments, the amount of the CAR-expressing immune cells is 85-115%, 90%-110%, or 95-105% that of the amount of the target cells.

In some embodiments, the incubation steps (a) and (b) are performed simultaneously. Simultaneous performance can allow for some difference between the start time and end time of these steps, e.g., by one hour, 30 minutes, or by 15 minutes. Performing steps (a) and (b) simultaneously can provide for conditions where the incubation time, the amount of the CAR-expressing immune cells and the amount of the target cells are substantially the same. In some embodiments, the determining steps (c) and (d) are performed simultaneously. Simultaneous performance can allow for some difference between the start time and end time of these steps, e.g., by one hour, 30 minutes, or by 15 minutes. Performing steps (c) and (d) simultaneously can provide for conditions where the incubation time, the amount of the CAR-expressing immune cells and the amount of the target cells are substantially the same.

In some embodiments, the method further comprises comparing the amount of interaction between the CAR-expressing immune cells and the target cells step (c) to the amount of the target cell death determined in a second control sample, wherein the target cells are incubated in the absence of the CAR-expressing immune cells.

In some embodiments, the method further comprises comparing the amount of interaction between the CAR-expressing immune cells and the target cells in step (c) to the amount of the target cell death determined in a third control sample, wherein the target cells are incubated in the absence of the CAR-expressing immune cells but in the presence of a detergent causing the target cell death. In certain embodiments, the detergent is Triton X-100.

In various embodiments, the target cells produce a detectable reporter signal upon said target cells death, and step (c) comprises determining the reporter signal in the test sample, step (d) comprises determining the reporter signal in the first control sample, and step (e) comprises comparing the reporter signals determined in steps (c) and (d). In some embodiments, the target cells express a reporter protein that produces a signal when the target cell interacts with the CAR-expressing immune cells.

In some embodiments, the reporter signal is luminescence. A protein that can generate the reporter signal (e.g., luminescence) may be expressed in a cell compartment. Upon cell death, the protein is released from the cell compartment into media, where the protein can generate a luminescent signal, such as by enzymatically acting upon an agent to generate luminescence. Exemplary cells that can be used in this manner include KILR® target cells. Target cells can be engineered to express an antigen that interacts with the chimeric antigen receptor. In certain embodiments, KILR® MM-1R Multiple Myeloma target cells are used. The target cells can also stably express a protein tagged with a label or enzyme. When the target cell line is used in a cytotoxicity assay, and its membrane is compromised due to cell death, the target cell line can release the tagged protein into the media. The tagged protein can be detected by adding to the media reagents that are substrates of the enzyme tag on the protein. For example, a beta-galactosidase enzyme can hydrolyze the substrate to give a chemiluminescent output. Luminescence can be quantified on a plate reader capable of measuring chemiluminescence. Alternatively, the tagged protein can be detected via assays for detecting the label.

In some embodiments, the reporter signal is fluorescence. A protein that can generate the reporter signal (e.g., fluorescence) may be expressed in a cell compartment. Upon cell death, the protein is released from the cell compartment into media, where the protein can generate a fluorescent signal.

In some embodiments, the inhibitory molecule specifically binds to the antigen on the target cells (e.g., tumor cells) which interacts with the CAR. Without wishing to be bound by theory, the use of an inhibitory molecule that binds to antigen can provide for a suitable control in a CAR potency assay such that untransfected or mock-transfected immune cells do not need to be used as a control. Such can eliminate the need to produce mock CAR-T cells in parallel to drug product. Production of mock CAR-T cells can impact drug product production in several ways. Eliminating the use of mock cell controls can simplify the manufacturing process is simplified, can ensure that patient dosing can be achieved by reducing sampling of any autologous CAR-T cells from the patient, and otherwise reduce cost in CAR-T cell therapy. The methods described herein can also reduce or eliminate testing delays due to mock cell failures. The method can also reduce testing errors through provision of a more simplified format. Reduction of testing delays and errors can also provide for avoidance of production delays and/or patient dosing delays.

In some embodiments, the inhibitory molecule specifically binds to the CAR. In some embodiments, the inhibitory molecule specifically binds to a region within the CAR that specifically binds to the antigen expressed on the target cells that interacts with the CAR. By binding to the CAR, particularly to a region within the CAR that specifically binds to the antigen (e.g., an epitope comprising one or more CDR sequences, or portions thereof), the inhibitory molecule can block the CAR-T cell from interacting with the target cell. Such blocking can prevent the CAR-T cell from interacting with the target cell. Thus, instead of using a mock transfected immune cell, the patient's own CAR-T cells can be used with addition of the inhibitory molecule as a suitable control instead.

In some embodiments, the inhibitory molecule is an antibody. In certain embodiments, the antibody is an anti-idiotype antibody. The anti-idiotype antibody can compete with the antigen on the host cell for binding to the chimeric antigen receptor. The anti-idiotype antibody can share some structural features with the antigen.

In some embodiments, the antibody or antibody fragment specifically binds to an antigen within the scFv domain of the chimeric antigen receptor. In some embodiments, the antibody or antibody fragment specifically binds to a CDR within the scFv domain. In some embodiments, the antibody or antibody fragment specifically binds to an antigen within the Fab domain of the chimeric antigen receptor. In some embodiments, the antibody or antibody fragment specifically binds to a CDR within the Fab domain. In some embodiments, the antibody or antibody fragment specifically binds to an antigen within the VH or the VL domain of the chimeric antigen receptor. In some embodiments, the antibody or antibody fragment specifically binds to a CDR within the VH or the VL domain.

In some embodiments, the inhibitory molecule is a soluble form of the antigen expressed on the target cells that interacts with the CAR, or a functional fragment or a derivative thereof.

In some embodiments, the immune cells are selected from T cells, induced pluripotent stem cells (iPSC) and natural killer (NK) cells. In some embodiments, the CAR interacts with a B-Cell maturation Antigen (BCMA) receptor, the target cells comprise the BCMA receptor and the inhibitory molecule is a soluble extracellular domain of BCMA. In some embodiments, the target cells are multiple myeloma cells. In certain embodiments, the multiple myeloma cells are MM-1R cells.

In various other embodiments, the CAR interacts with tumor and disease antigens that include, but are not limited to, BCMA, GPRC5D, CD79, KLK2, CD19, CD30, CD33, CD123, and FLT3.

In some embodiments, the CAR interacts with the tumor antigen GPRC5D. In some embodiments, the GPRC5D receptor is expressed by the target cells. In some embodiments, the inhibitory molecule is an anti-idiotype antibody or antibody fragment to the CAR. In some embodiments, the inhibitory molecule is an anti-idiotype antibody or antibody fragment to the GPRC5D receptor. As a non-limiting example, the target cells are multiple myeloma cells. A non-limiting example of a multiple myeloma cells are MM-1R cells.

In some embodiments, the CAR interacts with the tumor antigen KLK2. In some embodiments, the KLK2 antigen is expressed by target cells. In some embodiments, the inhibitory molecule is a soluble KLK2 protein. As a non-limiting example, the target cells are prostate cancer cells. A non-limiting example of a prostate cells are LNCaP cells.

Instead of using mock transfected CAR-T cells as a control when determining the level of antigen-specific cytotoxicity, the same CAR-T cells tested in the assay may be treated with an inhibitory molecule as described herein. Treatment with the inhibitory molecule (e.g., a monoclonal antibody or a soluble antigen to which the CAR specifically binds) can prevent the CAR-T cell from binding to the antigen and exerting cytotoxicity. Detection of an increase in the level of cytotoxicity of the antigen-specific stimulated cell, as compared to that of the same CAR-T cell treated with the inhibitory molecule, or a non-specifically stimulated CAR-T cell (i.e., a stimulated CAR-T cells that is not stimulated in an antigen-specific manner), can be used to indicate a stimulated CAR-T cell for use in therapy. The methods can be carried out in vitro.

In various embodiments, the inhibitory molecule (e.g., a tumor antigen or anti-idiotypic antibody) is not effective to stimulate the CAR-T cell that can be stimulated by an antigen (e.g., a tumor antigen) for which the CAR on the CAR-T cell is specific. Such embodiments can provide for the advantage of not activating a potency parameter that arises from activation of the CAR-T cell.

Also provided are methods for determining the potency and cytotoxic function of CAR-T cells. Generally, the methods include antigen-specific stimulation of the CAR on a CAR-T cell, followed by quantification of antigen-specific CAR-T cell cytotoxicity. A measure of CAR-T cell potency can be used as an in vitro indication of the expected in vivo pharmacokinetics of a CAR-T cell therapy product. Assays of CAR-T potency can further be used to determine whether a CAR-T cell product is suitable for clinical use, to assess potential efficacy of the CAR-T cell product, to determine dosage of CAR-T cells administered, and/or to characterize new manufacturing approaches for CAR-T cell therapy products.

The potency of a CAR-T cell therapy product can be expressed in terms reflecting the level of antigen-specific cytotoxicity of the product. This level of cytotoxicity can be compared, for example, to the level of cytotoxicity of a control sample of the CAR-T cell therapy product that is exposed to both antigen-specific stimulation as well as an inhibitory molecule described herein. Furthermore, the calculations can be normalized based on, for example, the number of cells in the test samples that express the CAR. Based on this information, a Cytotoxicity Index (CI) according to the following expression can be used as a measure of CAR-T cell therapy product potency:

$$CI=[(\text{cytotoxicity in stimulated group})-(\text{cytotoxicity in control group})]/\%\ \text{cells expressing CAR}$$

Methods known in the art can be used to determine the percentage of cells expressing the CAR (e.g., the level of transduction), for the normalization. For example, in tests utilizing flow cytometry, antibodies against the CAR can be included in the assay and used to quantify the level of CAR expressing cells, relative to the total number of T cells.

The level of antigen-specific in vitro cytotoxicity of CAR-T cell therapy products can correlate with in vivo pharmacokinetic (PK) and pharmacodynamics (PD) properties of the CAR-T products. PK/PD features of a CAR-T cell preparation that can be considered, according to the invention, include, for example, the Cmax, Tmax, and Area Under the Curve (AUC), which can be determined in clinical samples using standard methods in the art. The relationship between in vitro cytotoxicity of a CAR-T cell therapy product, as reflected in, e.g., a cytotoxicity index as described above, and the in vivo PK/PD characteristics of the product, can be shown using standard methods such as, for example, the Spearman correlation coefficient method, which can be used to assess linear associations between these features. Various methods described herein can provide a basis for predicting PK/PD parameters, based on antigen-specific in vitro cytotoxicity as shown, e.g., by determination of a CI.

Kits

Any of the compositions described herein may be comprised in a kit. In some embodiments, CAR-binding antibodies are provided in the kit, which also may include reagents suitable for expanding the cells, such as media, APCs, growth factors, antigens, other antibodies (e.g., for sorting or characterizing CAR T-cells) and/or plasmids encoding CARs or transposase.

In a non-limiting example, a CAR-binding antibody, a chimeric receptor expression construct (or reagents to generate a chimeric receptor expression construct), reagents for transfection of the expression construct, and/or one or more instruments to obtain allogeneic cells for transfection of the expression construct (such an instrument may be a syringe, pipette, forceps, and/or any such medically approved apparatus) are provided in a kit. In some aspects, the kit comprises reagents or apparatuses for electroporation of cells.

The kit may comprise target cells expressing an antigen that specifically interacts with the CAR-binding antibody, reagents for transfection of an expression construct encoding the antigen, and/or one or more instruments to obtain allogeneic cells for transfection of the expression construct (such an instrument may be a syringe, pipette, forceps, and/or any such medically approved apparatus) are provided in a kit. In some aspects, the kit comprises reagents or apparatuses for electroporation of cells.

The kit may comprise one or more suitably aliquoted compositions of the present invention or reagents to generate compositions of the invention. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the present invention also will typically include a means for containing the chimeric receptor construct and any other reagent containers in close confinement for commercial sale. Such containers may include injection or blow molded plastic containers into which the desired vials are retained, for example.

EMBODIMENTS

1. An in vitro method for determining potency of an immune cell expressing a chimeric antigen receptor (CAR) molecule, the method comprising:

a) in a test sample, contacting the CAR-expressing immune cells with target cells, wherein the target cells express an antigen which interacts with the CAR, b) in a first control sample, contacting the CAR-expressing immune cells with the target cells, wherein (i) said contacting is conducted in the presence of an inhibitory molecule or (ii) the CAR-expressing immune cells and/or the target cells have been pre-incubated with the inhibitory molecule prior to said contacting, wherein the inhibitory molecule inhibits the interaction between the CAR and the target cells, c) determining the amount of the target cell death in the test sample, d) determining the amount of the target cell death in the first control sample, and e) determining potency of CAR-expressing immune cells based on comparing the amount of the target cell death determined in steps (c) and (d), wherein the contacting time, the amount of the CAR-expressing immune cells and the amount of the target cells are substantially the same in the test sample and the first control sample.

2. The method of embodiment 1, wherein the contacting steps (a) and (b) are performed simultaneously.

3. The method of embodiment 1 or embodiment 2, wherein the determining steps (c) and (d) are performed simultaneously.

4. The method of any one of embodiments 1-3, wherein in step (b)(i) the CAR-expressing immune cells and/or the target cells have been pre-incubated with the inhibitory molecule prior to the contacting step.

5. The method of any one of embodiments 1-4, wherein said method further comprises comparing the amount of the target cell death determined in step (c) to the amount of the target cell death determined in a second control sample, wherein the target cells are incubated in the absence of the CAR-expressing immune cells.

6. The method of any one of embodiments 1-5, wherein said method further comprises comparing the amount of the target cell death determined in step (c) to the amount of the target cell death determined in a third control sample, wherein the target cells are incubated in the absence of the CAR-expressing immune cells but in the presence of a detergent causing the target cell death.

7. The method of embodiment 6, wherein the detergent is Triton X-100.

8. The method of any one of embodiments 1-7, wherein the target cells produce a detectable reporter signal upon said target cell death, and step (c) comprises determining the reporter signal in the test sample, step (d) comprises determining the reporter signal in the first control sample, and step (e) comprises comparing the reporter signals determined in steps (c) and (d).

9. The method of embodiment 8, wherein the reporter signal is luminescence.

10. The method of embodiment 8, wherein the reporter signal is fluorescence.

11. The method of any one of embodiments 8-10, wherein the target cells express a reporter protein that produces a signal when the target cell undergoes cell death.

12. The method of embodiment 11, wherein the reporter protein is beta-galactosidase, luciferase, Green Fluorescent Protein (GFP), or a variant or derivative thereof.

13. The method of any one of embodiments 1-12, wherein the inhibitory molecule specifically binds to the antigen on the target cells which antigen interacts with the CAR.

14. The method of any one of embodiments 1-13, wherein the inhibitory molecule specifically binds to the CAR.

15. The method of embodiment 14, wherein the inhibitory molecule specifically binds to a region within the CAR that specifically binds to the antigen expressed on the target cells.

16. The method of embodiment 13, 14 or 15, wherein the inhibitory molecule is an antibody or antibody fragment.

17. The method of embodiment 16, wherein the antibody is an anti-idiotype antibody.

18. The method of embodiment 16 or 17, wherein the antibody fragment is Fab, Fab', $F(ab')_2$, a Fv or Fd fragment, a single chain antibody (scFv), a linear antibody, a single domain antibody, a heavy chain variable region (VH) domain, or a light chain variable region (VL) domain.

19. The method of embodiment 16, 17 or 18, wherein the antibody or antibody fragment specifically binds to an antigen within the scFv domain of the CAR.

20. The method of embodiment 19, wherein the antibody or antibody fragment specifically binds to a complementarity determining region (CDR) within the scFv domain of the CAR.

21. The method of embodiment 16, 17 or 18, wherein the antibody or antibody fragment specifically binds to an antigen within the VH domain or the VL domain of the CAR.

22. The method of embodiment 21, wherein the antibody or antibody fragment specifically binds to a CDR within the VH domain or the VL domain of the CAR.

23. The method of embodiment 14 or 15, wherein the inhibitory molecule is a soluble form of the antigen expressed on the target cells that interact with the CAR, or a functional fragment or a derivative thereof.

24. The method of any one of embodiments 1-23, wherein the immune cells are selected from T cells, induced pluripotent stem cells (iPSC) and natural killer (NK) cells.

25. The method of any one of embodiments 1-24, wherein the CAR interacts with a B-Cell maturation Antigen (BCMA) receptor, the target cells comprise the BCMA receptor and the inhibitory molecule is a soluble extracellular domain of BCMA.

26. The method of embodiment 25, wherein the target cells are multiple myeloma cells.

27. The method of embodiment 26, wherein the multiple myeloma cells are MM-1R cells.

28. The method of any one of embodiments 1-24, wherein the CAR interacts with a G protein-coupled receptor, class C group 5 member D (GPRC5D), the target cells comprise the GPRC5D receptor and the inhibitory molecule is an anti-idiotype antibody or antibody fragment to the CAR.

29. The method of any one of embodiments 1-24, wherein the CAR interacts with a G protein-coupled receptor, class C group 5 member D (GPRC5D), the target cells comprise the GPRC5D receptor and the inhibitory molecule is an anti-idiotype antibody or antibody fragment to the GPRC5D receptor.

30. The method of embodiment 28 or 29, wherein the target cells are multiple myeloma cells.

31. The method of embodiment 30, wherein the multiple myeloma cells are MM-1R cells.

32. The method of any one of embodiments 1-24, wherein the CAR interacts with kallikerin 2 (KLK2), the target cells comprise the KLK2 and the inhibitory molecule is a soluble KLK2 protein.

33. The method of embodiment 32, wherein the target cells are prostate cancer cells.

34. The method of embodiment 33, wherein the prostate cancer cells are LNCaP cells.

35. The method of any one of embodiments 1-34, wherein the method is conducted in a high throughput format.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

The following materials were used in this example. CAR-T DP samples were used as the test material, with KILR® MMI-R® reporter cells (cat #97-1045P052, Eurofins Discoverx Corp., Fremont, CA) used as the target cell line. KILR® MM-1R® cells express an enhanced Prolabel (ePL) tagged housekeeping gene. Once the cells have been lysed, the ePL-tagged protein is released into the media. Addition of an enzyme acceptor will cause the complementation of the β-galactosidase enzyme fragments, EA and ePL. The resulting functional enzyme will hydrolyze its substrate to generate a chemiluminescent signal.

KILR MM-1R® cells were grown in RPMI 1640 (ATCC formulation) (Gibco cat #A10491-01, ThermoFisher, Waltham, MA) with 10% HI-FBS (6140-071, Life Technologies, Carlsbad, CA), and 250 μg/mL G418 Sulfate (Corning cat #30-234-CR, ThermoFisher, Waltham, MA). Assays were executed in an assay medium composed of RPMI 1640 with L-Glutamine and 25 mM HEPES (Corning Cat No. 10-041-CV, ThermoFisher, Waltham, MA) and 10% HI-FBS (6140-071, Life Technologies, Carlsbad, CA).

Soluble Human BCMA Protein (sBCMA), (BCA-H522y, Acro Biosystems, Newark DE) the blocking protein, was formulated in assay medium. A solution of 10% TritonX-100 (cat #93443-100ML, SigmaAldrich Co., St. Louis, Mo) was used to make the total death control. Cell cytotoxicity was detected using KILR® Detection™ kit, (cat #97-001, Eurofins Discoverx Corp., Fremont, CA).

In the example, the ability of CAR-T cell Drug Product (DP) to kill multiple myeloma target cells expressing the relevant antigen was measured. Target cells were used which expressed reporter genes that produced a measurable signal (for example luminescence) due to cell death when bound by the effector CAR-T cells. The results were presented in an activity measurement that was used to determine if the DP demonstrated the appropriate level of activity for release.

The assay was comprised of four components used in a total of 16 wells. The four components used were (i) the CAR-T Drug Product (DP) with Target cells (total activity), (ii) the CAR-T DP cells blocked by the blocking reagent with Target cells (baseline control), (iii) the Target cells with medium (no cell death control), and (iv) the target cells with 0.1% TitonX-100 (total cell death control). All four assay components were run as four individual replicates, as shown in the plate layout of Table 1A below. The detailed description of the samples in the 96 well plate is provided in Table 1B. One 96-well plate was used to run six assays, one of which was an assay of a QC CAR-T cell used for system suitability and to trend method performance. The QC CAR-T cells were previously qualified for activity.

TABLE 1A

96 Well Assay Plate Layout

| | 1 | 2 | 3 | 4 | 5 | 6 | 7 | 8 | 9 | 10 | 11 | 12 |
|---|---|---|---|---|---|---|---|---|---|---|---|---|
| A | KILR | KILR | CAR-T | Baseline | KILR | KILR | CAR-T | Baseline | KILR | KILR | CAR-T | Baseline |
| B | MM-1R+ | MM-1R | Sample | Control | MM-1R+ | MM-1R | Sample | Control | MM-1R+ | MM-1R | Sample | Control |
| C | TritonX- | only | 1 | 1 | TritonX- | only | 3 | 3 | TritonX- | only | 5 | 5 |
| D | 100 | | | | 100 | | | | 100 | | | |
| E | KILR | KILR | CAR-T | Baseline | KILR | KILR | CAR-T | Baseline | KILR | KILR | CAR-T | Baseline |
| F | MM-1R+ | MM-1R | Sample | Control | MM-1R+ | MM-1R | Sample | Control | MM-1R+ | MM-1R | Sample | Control 6 |
| G | TritonX- | only | 2 | 2 | TritonX- | only | 4 | 4 | TritonX- | only | 6 | |
| H | 100 | | | | 100 | | | | 100 | | | |

TABLE 1B

| Description of Samples in 96 Well Assay Plate |
|---|
| Sample 1: |
| Col. 1, Row A-D KILR ® MM-1R + 0.1% TritonX-100 control (total cell death) |
| Col. 2, Row A-D KILR ® MM-1R cells only (no cell death) |
| Col. 3, Row A-D Sample 1 CAR-T cells at 5:1 E:T |
| Col. 4, Row A-D Sample 1 Blocked CAR-T cells at 5:1 E:T (baseline control) |
| Sample 2: |
| Col. 5, Row A-D KILR ® MM-1R + 0.1% TritonX-100 control (total cell death) |
| Col. 6, Row A-D KILR ® MM-1R cells only (no cell death) |
| Col. 7, Row A-D Sample 2 CAR-T cells at 5:1 E:T |
| Col. 8, Row A-D Sample 2 Blocked CAR-T cells at 5:1 E:T (baseline control) |
| Sample 3: |
| Col. 9, Row A-D KILR ® MM-1R + 0.1% TritonX-100 (total cell death) |
| Col. 10, Row A-D KILR ® MM-1R cells only (no cell death) |
| Col. 11, Row A-D Sample 3 CAR-T cells at 5:1 E:T |
| Col. 12, Row A-D Sample 3 Blocked CAR-T cells at 5:1 E:T (baseline control) |
| Sample 4: |
| Col. 1, Row E-H KILR ® MM-1R + 0.1% TritonX-100 (total cell death) |
| Col. 2, Row E-H KILR ® MM-1R cells only (no cell death) |
| Col. 3, Row E-H Sample 4 CAR-T cells at 5:1 E:T |
| Col. 4, Row E-H Sample 4 Blocked CAR-T cells at 5:1 E:T (baseline control) |
| Sample 5: |
| Col. 5, Row E-H KILR ® MM-1R + 0.1% TritonX-100 (total cell death) |
| Col. 6, Row E-H KILR ® MM-1R cells only (no cell death) |
| Col. 7, Row E-H Sample 5 CAR-T cells at 5:1 E:T |
| Col. 8, Row E-H Sample 5 Blocked CAR-T cells at 5:1 E:T (baseline control) |
| Sample 6: |
| Col. 9, Row E-H KILR ® MM-1R + 0.1% TritonX-100 (total cell death) |
| Col. 10, Row E-H KILR ® MM-1R cells only (no cell death) |
| Col. 11, Row E-H Sample 6 CAR-T cells at 5:1 E:T (QC CAR-T control) |
| Col. 12, Row E-H Sample 6 Blocked CAR-T cells at 5:1 E:T (baseline control) |

The following assay conditions were used for LCAR-B38M CAR-T DP and KILR® MM-1R Multiple Myeloma target cells (Eurofins Discoverx Corp., Fremont, CA). The assay medium was RPMI1640 and 10% HI-FBS. KILR® MM-1R cells were grown as specified by the manufacturer. Baseline controls were generated by blocking the LCAR-B38M DP cells with the soluble extracellular domain of B-Cell maturation Antigen (sBCMA). The KILR® detection kit (Eurofins Discoverx Corp., Fremont CA) was used as the assay detection reagent. Optimization was performed on the effector cell (DP) to target cell (ex. KILR® MM-1R) ratio (E:T), as well as the amount of blocking reagent needed to fully block the interaction between the CAR-T cells (DP) and their target cells. The E:T ratio and blocking reagent concentration were optimized for each drug product and its corresponding target cell line. Once established, the E:T ratio was fixed in assay and remains fixed for all drug product testing. Blocking regent was qualified for each lot and used at that level for drug product testing. Additionally, detection conditions may be optimized based on the reporter system used.

An assay of the LCAR-B38M CAR-T drug product was performed as follows in 96 well white opaque TC treated assay plates. Each assay plate accommodated up to 6 assays, as described in Table 1A above. For each assay, 25 μL of blocking reagent was added to the blocked CAR-T cell wells (baseline control) of the assay plate, followed by the addition of 25 μL of assay medium into CAR-T test wells. Next, 25 μL CAR-T DP cells were added at $8\times10^5$ viable cells/mL (for a total of $2\times10^4$ viable cells/well) into the CAR-T test wells and baseline control wells. 50 μL of assay medium was added to the KILR MM-1R cell only (no cell death) wells. The contents of the wells were mixed gently and incubated for 10 min. (±5 min.) at 37° C., 5% $CO_2$, and humidified.

Upon completion of the incubation, 50 μL of target cells at $8\times10^4$ viable cells/mL were added to all assay wells (final $4\times10^3$ viable cells/well), which resulted in a final E:T ratio of 5:1. In each assay, the last addition was 0.1% Triton X-100 (50 μL/well) to the total cell death control wells. The contents of the wells were incubated at 37° C., 5% $CO_2$, and humidified for 22 hours (±1 hour). Upon completion of the co-culture incubation, assay plates were removed from the incubator and allowed to equilibrate at room temperature for 30 minutes (+/−5 minutes). The detection reagent was thawed and then equilibrated to room temperature for 30 minutes at the same time. Once equilibrated, 100 μL of KILR® detection reagent was added per well, and incubated with protected from light for 50 minutes (+/−5 minutes). The plate was read on a Molecular Devices Paradigm plate reader set for chemiluminescence after a 10 second shake.

The data are shown below in Tables 2 and 3. The data of Table 2 show a lot titration of sBCMA protein demonstrating BCMA blocking of LCAR-B38M killing of KILR MM-1R Multiple Myeloma target cells ranging from 50-400 μg/mL. The data of Table 3 demonstrate sBCMA blocking specificity for Multiple Myeloma Target cells (RPMI8226_Luc) as compared with non-B cell target cells (K562_luc cells).

TABLE 2

BCMA titration demonstrating protein blocking CAR-T cells activity on Target cells.

| Sample ID | % CAR-T Killing | % RSD |
|---|---|---|
| 400 ug/mL lot C108P1-86BF2-NX | 62% | 1% |
| 300 ug/mL lot C108P1-86BF2-NX | 79% | 1% |
| 250 ug/mL lot C108P1-86BF2-NX | 79% | 1% |
| 200 ug/mL lot C108P1-86BF2-NX | 74% | 1% |
| 150 ug/mL lot C108P1-86BF2-NX | 68% | 2% |
| 100 ug/mL lot C108P1-86BF2-NX | 59% | 3% |
| 50 ug/mL lot C108P1-86BF2-NX | 42% | 5% |

TABLE 3

Demonstration of specificity for Multiple Myeloma vs. non-B cell line.

| Test Method | Sample ID | % CAR-T Killing | % Control T Cell Killing | % Total Killing |
|---|---|---|---|---|
| Blocking | SH19-28/RPMI8226_Luc | 29% | 53% | 67% |
| Blocking | SH19-28/K562_Luc | −41% | 39% | 13% |
| Blocking | PQ-0330 Donor B MOI = 1.5/ RPMI8226_luc | 28% | 67% | 77% |
| Blocking | PQ-0330 Donor B MOI = 1.5/ K562_Luc | −46% | 43% | 18% |

Example 2

GPRC5D CAR-T cells were tested using an anti-ID antibody to the CAR of the CAR-T cells. The assay condition for GPRC5D CAR-T cells are like those used for LCAR-B38M in Example 1 above. For GPRC5D CAR-T, another multiple myeloma target, the same KILR MM-1R target cells are used. The assay medium, and detection reagents are the same as those used in Example 1. The 5:1 E:T ratio and the seeding densities are the same as in Example 1. The blocking reagent is a GCPR5D anti-idiotype antibody to the GPRC5D CAR. Examples of GCPR5D anti-idiotype antibodies for use in the assay include GP5B337, GP5B332, GP5B324 and GP5B206. The heavy chain and light chain sequences of these anti-idiotype antibodies are provided in Table 5. Incubation times were aligned with those of Example 1 above. All other reagents are the same as those used in Example 1. Initial titration studies shown below in Table 4 indicate blocking of GPRC5D CAR-T cells with the anti-ID antibody (GP5B337).

TABLE 4

GPRC5D CAR-T Titration Data.

| Sample # | Test Method | Sample ID | % CAR-T Killing |
|---|---|---|---|
| 1 | Mocks | SH-5D-19-25 w/Mocks | 80% |
| 2 | Mocks | SH-5D-19-25 w/Mocks | 79% |
| 3 | anti-ID Blocking | SH-5D-19-25 w/200 ug/mL anti-ID (1.61 mg/mL) | 52% |
| 4 | anti-ID Blocking | SH-5D-19-25 w/200 ug/mL anti-ID (1.01 mg/mL) | 74% |
| 5 | anti-ID Blocking | SH-5D-19-25 w/100 ug/mL anti-ID (1.61 mg/mL) | 48% |
| 6 | anti-ID Blocking | SH-5D-19-25 w/100 ug/mL anti-ID (1.01 mg/mL) | 53% |
| 7 | anti-ID Blocking | SH-5D-19-25 w/50 ug/mL anti-ID (1.61 mg/mL) | 41% |
| 8 | anti-ID Blocking | SH-5D-19-25 w/50 ug/mL anti-ID (1.01 mg/mL) | 38% |
| 9 | anti-ID Blocking | SH-5D-19-25 w/25 ug/mL anti-ID (1.61 mg/mL) | 38% |
| 10 | anti-ID Blocking | SH-5D-19-25 w/25 ug/mL anti-ID (1.01 mg/mL) | 31% |
| 11 | anti-ID Blocking | SH-5D-19-25 w/12.5 ug/mL anti-ID (1.61 mg/mL) | 30% |
| 12 | anti-ID Blocking | SH-5D-19-25 w/12.5 ug/mL anti-ID (1.01 mg/mL) | 23% |
| 13 | anti-ID Blocking | SH-5D-19-25 w/6.25 ug/mL anti-ID (1.61 mg/mL) | 22% |
| 14 | anti-ID Blocking | SH-5D-19-25 w/6.25 ug/mL anti-ID (1.01 mg/mL) | 20% |
| 15 | anti-ID Blocking | SH-5D-19-25 w/3.13 ug/mL anti-ID (1.61 mg/mL) | 24% |
| 16 | anti-ID Blocking | SH-5D-19-25 w/3.13 ug/mL anti-ID (1.01 mg/mL) | 18% |
| 17 | anti-ID Blocking | SH-5D-19-25 w/1.56 ug/mL anti-ID (1.61 mg/mL) | 16% |
| 18 | anti-ID Blocking | SH-5D-19-25 w/1.56 ug/mL anti-ID (1.01 mg/mL) | 17% |

TABLE 5

| Heavy chain and light chain sequences for exemplary GCPR5D anti-idiotype antibodies |
|---|
| GP5B337 heavy chain (SEQ ID NO: 1)<br>QVQLVQSGAEVKKPGSSVKVSCKASGGTFSSYAISWVRQAPGQGLEWMGGIIPIFGTANY<br>AQKFQGRVTITADESTSTAYMELSSLRSEDTAVYYCARTSVEALDYWGQGTLVTVSSAKT<br>TAPSVYPLAPVCGDTTGSSVTLGCLVKGYFPEPVTLTWNSGSLSSGVHTFPAVLQSDLYT<br>LSSSVTVISSTWPSQSITCNVAHPASSTKVDKKIEPRGPTIKPCPPCKCPAPNLLGGPSV<br>FIFPPKIKDVLMISLSPIVTCVVVDVSEDDPDVQISWFVNNVEVHTAQTQTHREDYNSTL<br>RVVSALPIQHQDWMSGKEFKCKVNNKDLPAPIERTISKPKGSVRAPQVYVLPPPEEEMTK<br>KQVTLTCMVTDFMPEDIYVEWTNNGKTELNYKNTEPVLDSDGSYFMYSKLRVEKKNWVER<br>NSYSCSVVHEGLHNHHTTKSFSRTPGK |
| GP5B337 light chain (SEQ ID NO: 2)<br>EIVLTQSPATLSLSPGERATLSCRASQSVSDDLAWYQQKPGQAPRLLIYIASNRATGIPA<br>RFSGSGSGTDFTLTISSLEPEDFAVYYCQQYIRAPFTFGQGTKVEIKRADAAPTVSIFPP<br>SSEQLTSGGASVVCFLNNFYPKDINVKWKIDGSERQNGVLNSWTDQDSKDSTYSMSSTLT<br>LTKDEYERHNSYTCEATHKTSTSPIVKSENRNEC |
| GP5B332 heavy chain (SEQ ID NO: 3)<br>EVQLLESGGGLVQPGGSLRLSCAASGFTFSSYAMSWVRQAPGKGLEWVSAISGSGGSTYY<br>ADSVKGRFTISRDNSKNTLYLQMNSLRAEDTAVYYCAKGGFPWDLAYALDYWGQGTLVTV<br>SSAKTTAPSVYPLAPVCGDTTGSSVTLGCLVKGYFPEPVTLTWNSGSLSSGVHTFPAVLQ<br>SDLYTLSSSVTVISSTWPSQSITCNVAHPASSTKVDKKIEPRGPTIKPCPPCKCPAPNLL<br>GGPSVFIFPPKIKDVLMISLSPIVTCVVVDVSEDDPDVQISWFVNNVEVHTAQTQTHRED<br>YNSTLRVVSALPIQHQDWMSGKEFKCKVNNKDLPAPIERTISKPKGSVRAPQVYVLPPPE<br>EEMTKKQVTLTCMVTDEMPEDIYVEWTNNGKTELNYKNTEPVLDSDGSYFMYSKLRVEKK<br>NWVERNSYSCSVVHEGLHNHHTTKSFSRTPGK |
| GP5B332 light chain (SEQ ID NO: 4)<br>DIQMTQSPSSLSASVGDRVTITCRASQSIGNYLNWYQQKPGKAPKLLIYDASSLQSGVPS<br>RFSGSGSGTDFTLTISSLQPEDFATYYCQQHYTFPFTFGQGTKVEIKRADAAPTVSIFPP<br>SSEQLTSGGASVVCFLNNFYPKDINVKWKIDGSERQNGVLNSWTDQDSKDSTYSMSSTLT<br>LTKDEYERHNSYTCEATHKTSTSPIVKSENRNEC |
| GP5B324 heavy chain (SEQ ID NO: 5)<br>EVQLLESGGGLVQPGGSLRLSCAASGFTFSSYAMSWVRQAPGKGLEWVSAINYDGSSTYY<br>ADSVKGRFTISRDNSKNTLYLQMNSLRAEDTAVYYCAKHGAFSSYALDYWGQGTLVTVSS<br>AKTTAPSVYPLAPVCGDTTGSSVTLGCLVKGYFPEPVTLTWNSGSLSSGVHTFPAVLQSD<br>LYTLSSSVTVTSSTWPSQSITCNVAHPASSTKVDKKIEPRGPTIKPCPPCKCPAPNLLGG<br>PSVFIFPPKIKDVLMISLSPIVTCVVVDVSEDDPDVQISWFVNNVEVHTAQTQTHREDYN<br>STLRVVSALPIQHQDWMSGKEFKCKVNNKDLPAPIERTISKPKGSVRAPQVYVLPPPEEE |

TABLE 5-continued

| Heavy chain and light chain sequences for exemplary GCPR5D anti-idiotype antibodies |
|---|
| MTKKQVTLTCMVTDEMPEDIYVEWTNNGKTELNYKNTEPVLDSDGSYFMYSKLRVEKKNW<br>VERNSYSCSVVHEGLHNHHTTKSFSRTPGK |
| GP5B324 light chain (SEQ ID NO: 6)<br>EIVLTQSPATLSLSPGERATLSCRASQSVADFLAWYQQKPGQAPRLLIYDASNRATGIPA<br>RFSGSGSGTDFTLTISSLEPEDFAVYYCQQSHRAPFTFGQGTKVEIKRADAAPTVSIFPP<br>SSEQLTSGGASVVCFLNNFYPKDINVKWKIDGSERQNGVLNSWTDQDSKDSTYSMSSTLT<br>LTKDEYERHNSYTCEATHKTSTSPIVKSENRNEC |
| GP5B206 heavy chain (SEQ ID NO: 7)<br>DVQLQESGPGLVAPSQSLSITCTVSGFSLTSYAISWVRQPPGKGLEWLGVIWTDGGTNYN<br>SALKSRLSISKDNSKSQVFLKMNSLQTDDTARYYCARREDSYGDLFAYWGQGTTVTVSSA<br>KTTAPSVYPLAPVCGDTTGSSVTLGCLVKGYFPEPVTLTWNSGSLSSGVHTFPAVLQSDL<br>YTLSSSVTVISSTWPSQSITCNVAHPASSTKVDKKIEPRGPTIKPCPPCKCPAPNLLGGP<br>SVFIFPPKIKDVLMISLSPIVTCVVVDVSEDDPDVQISWFVNNVEVHTAQTQTHREDYNS<br>TLRVVSALPIQHQDWMSGKEFKCKVNNKDLPAPIERTISKPKGSVRAPQVYVLPPPEEEM<br>TKKQVTLTCMVTDEMPEDIYVEWTNNGKTELNYKNTEPVLDSDGSYFMYSKLRVEKKNWV<br>ERNSYSCSVVHEGLHNHHTTKSFSRTPGK |
| GP5B206 light chain (SEQ ID NO: 8)<br>DIVMTQSPAILSVSPGERVSFSCRASQSIGTNIHWYQQRINGSPRLLIKYASESISGIPS<br>RFSGSGSGTDFTLSINSVESEDIADYYCQQTNTWPLTFGAGTKLELKRADAAPTVSIFPP<br>SSEQLTSGGASVVCFLNNFYPKDINVKWKIDGSERQNGVLNSWTDQDSKDSTYSMSSTLT<br>LTKDEYERHNSYTCEATHKTSTSPIVKSENRNEC |

Example 3

GPRC5D CAR-T cells were tested using an anti-ID antibody Fab fragment to the CAR of the CAR-T cells. The assay condition for GPRC5D CAR-T cells were like those used for LCAR-B38M in Example 1 above. For GPRC5D CAR-T, another multiple myeloma target, the same KILR MM-1R target cells were used. The assay medium, and detection reagents were the same as those used in Examples 1 and 2. The 5:1 E:T ratio and the seeding densities were the same as in Examples 1 and 2. The blocking reagent was a GCPR5D anti-idiotype Fab antibody (GP5B337) fragment to the GPRC5D CAR. Incubation times were aligned with those of Examples 1 and 2 above. All other reagents were the same as those used in Examples 1 and 2. Initial titration studies shown below in Table 6 indicate blocking of GPRC5D CAR-T cells with the anti-ID Fab antibody (GP5B337) fragment.

TABLE 6

GPRC5D CAR-T Anti-ID Fab fragment Titration Data

| Sample # | Test Method | Sample ID | % CAR-T Killing |
|---|---|---|---|
| 1 | Mocks | SH20-5D-021 w/Mocks | 70% |
| 3 | anti-ID Fab Blocking | SH20-5D-021 w/ 300 ug/mL anti-ID | −11% |
| 5 | anti-ID Fab Blocking | SH20-5D-021 w/ 150 ug/mL anti-ID | 37% |
| | anti-ID Fab Blocking | SH20-5D-021 w/ 75 ug/mL anti-ID | 58% |
| 6 | anti-ID Fab Blocking | SH20-5D-021 w/ 37.5 ug/mL anti-ID | 34% |

The GPRC5D anti-idiotype Fab fragment was generated from the full length anti-idiotype antibody to the GPRC5D CAR using the Pierce Fab Preparation Kit (ThermoFisher, Catalog #: VF299292) following the kit procedure with minor adjustments. Briefly, BupH Phosphate Buffered Saline (PBS) and digestion buffer were prepared. IgG was removed from the refrigerator, diluted with the prepared PBS, and ran through the desalting columns. Eluent was collected and transferred over to the prepared Papain Digestion Columns for digestion at 37° C. After about 5 hours of digestion and rotating at 37° C., the tubes were removed from the incubator and spun down to collect sample. Kit Protein A columns were prepared, sample was added, and columns were rotated overnight at 2-8° C. for about 20 hours. Protein A columns were spun down to collect sample in Fractions. The first and second fractions were collected, combined and stored. Previous work such as A280 and 1D Silver Stains have shown that those fractions contained the most desired fragment. Fresh Protein A columns were prepared (not used previously) and sample was added once again for a secondary 2-8° C. rotation that lasted about 1 hour. The second Protein A incubation was added to further purify and remove any possible Fc region contaminations that was thought to be having an effect on Bioassays. Fragments were eluted, concentrated in 10K Amicon tubes (Cat UFC501008) and stored at 2-8° C.

Example 4

GPRC5D CAR-T cells are tested using an anti-GPRC5D antibody or its Fab fragment to the antigen of the CAR-T cells (GPRC5D receptor). The assay condition for GPRC5D CAR-T cells is like those used for GPRC5D CAR-T DP in Example 2 above. For GPRC5D CAR-T, another multiple myeloma target, the same KILR MM-1R target cells are used. The assay medium, and detection reagents are the same as those used in Examples 2 and 3. The 5:1 E:T ratio and the seeding densities are the same as in Examples 2 and 3. The blocking reagent is an anti-GCPR5D antibody or its Fab antibody fragment. These blocking reagents bind to the GPRC5D receptors on the KILR MM-1R target cells and inhibit the ability of the CAR-T cell to bind its target. The anti-GPRC5D antibody Fab is generated from the full length anti-GPRC5D antibody using established methods as detailed above. Incubation times are aligned with those of Examples 2 and 3. All other reagents are the same as those used in Examples 2 and 3. Initial titration studies shown below in Table 7 indicate blocking of KILR MM-1R cells with the anti-GPRC5D antibody or Fab fragment.

TABLE 7

GPRC5D CAR-T Anti-ID Fab fragment Titration Plan

| Sample # | Test Method | Sample ID |
|---|---|---|
| 1 | Mocks | GPRC5D CAR-T DP w/Mocks |
| 2 | anti-GPRC5D antibody or Fab Blocking | GPRC5D CAR-T DP w/ 500 ug/mL anti-GPRC5D antibody or Fab |
| 3 | anti-GPRC5D antibody or Fab Blocking | GPRC5D CAR-T DP w/ 400 ug/mL anti-GPRC5D antibody or Fab |
| 4 | anti-GPRC5D antibody or Fab Blocking | GPRC5D CAR-T DP w/ 300 ug/mL anti-GPRC5D antibody or Fab |
| 5 | anti-GPRC5D antibody or Fab Blocking | GPRC5D CAR-T DP w/ 200 ug/mL anti-GPRC5D antibody or Fab |
| 6 | anti-GPRC5D antibody or Fab Blocking | GPRC5D CAR-T DP w/ 100 ug/mL anti-GPRC5D antibody or Fab |
| 7 | anti-GPRC5D antibody or Fab Blocking | GPRC5D CAR-T DP w/ 50 ug/mL anti-GPRC5D antibody or Fab |
| 8 | anti-GPRC5D antibody or Fab Blocking | SH20-5D-021 w/ 37.5 ug/mL anti-ID |

Example 5

KLK2 CAR-T cells were tested using human soluble KLK2 protein to the CAR of the CAR-T cells. The assay condition for KLK2 CAR-T cells was like those used for LCAR-B38M in Example 1 above. KLK2 CAR-T targets kallikerin 2 (KLK2) a molecule expressed on malignant luminal prostate. An overexpressed KLK2 reporter cell line was generated using LNcaP cells (ATCC, CRL1740) and the DiscoverX's Killing Immune-Lysis Reaction (KILR) reporter. The killing principle is the same as described in Example 1. These cells expressed an enhanced Prolabel (ePL) tagged housekeeping gene, once lysed, the tagged reporter protein was released into the media. Addition of enzyme acceptor caused the complementation of the β-galactosidase enzyme fragments, EA and ePL. The resulting functional enzyme hydrolyzed its substrate to generate a chemiluminescent signal. The assay medium, detection reagents and the target seeding densities are all the same as those used in Example 1, but the E:T ratio was 10:1. The blocking reagent was a soluble protein to the KLK2 CAR. The amino acid sequence of this soluble KLK2 protein with C-terminal His6 tag (SEQ ID NO: 12) is provided below (underlined sequence is the signal peptide):

```
                                        (SEQ ID NO: 9)
MWDLVLSIALSVGCTGAVPLIEGRIVGGWECEKHSQPWQVAVYSHGWAH

CGGVLVHPQWVLTAAHCLKKNSQVWLGRHNLFEPEDTGQRVPVSHSFPH

PLYNMSLLKHQSLRPDEDSSHDLMLLRLSEPAKITDVVKVLGLPTQEPA

LGTTCYASGWGSIEPEEFLRPRSLQCVSLHLLSNDMCARAYSEKVTEFM

LCAGLWTGGKDTCGGDSGGPLVCNGVLQGITSWGPEPCALPEKPAVYTK

VVHYRKWIKDTIAANPHHHHHH
```

KILR LNcaP-KLK2 cells were grown in RPMI 1640 (Gibco cat #11875-093, ThermoFisher, Waltham, MA) with 10% FBS (97068-085, VWR, Radnor, PA), and 250 μg/mL G418 Sulfate (Corning cat #30-234-CR, Corning, Tewksbury, MA). Assays were executed in an assay medium composed of RPMI 1640 with L Glutamine (Corning Cat No. 10-040-CV, Corning, Tewksbury, MA) and 10% FBS (97068-085, VWR, Radnor, PA).

Even though the target cell line in this Example was different than in Examples 1 and 2, the strategy and set up were similar to Examples 1 and 2.

The following assay conditions were used for KLK2 CAR-T DP and KILR LNcaP-KLK2 target cells. The assay medium was RPMI1640 and 10% HI-FBS. KILR LNcaP-KLK2 cells were grown in RPMI1640 and 10% FBS, 1× non-essential amino acids, 2.5 μg/mL puromycin and 500 μg/mL G418 sulfate. Baseline controls and the optimization of the assay followed Example 1. Baseline controls were generated by blocking the KLK2 CAR-T DP cells with the soluble human KLK2 protein (sKLK2). The KILR® detection kit (Eurofins Discoverx Corp., Fremont CA) was used as the assay detection reagent. Optimization was performed on the effector cell (DP) to target cell (ex. KILR LNcaP-KLK2) ratio (E:T), as well as the amount of blocking reagent needed to fully block the interaction between the CAR-T cells (DP) and their target cells. The E:T ratio and blocking reagent concentration were optimized for each drug product and its corresponding target cell line. Once established, the E:T ratio was fixed in the assay and remained fixed for all drug product testing. Blocking reagent was qualified for each lot and used at that level for drug product testing. Additionally, detection conditions were optimized based on the reporter system used.

The KLK2 CAR-T drug product assay was performed as in Example 1, in 96 well white opaque TC treated assay plates. The assay steps as follows, each assay plate accommodated up to 6 assays, as described in Table 1A Example 1. For each assay, 25 μL of blocking reagent was added to the blocked CAR-T cell wells (baseline control) of the assay plate, followed by the addition of 25 μL of assay medium into CAR-T test wells. Next, 25 μL CAR-T DP cells were added at $1.6\times10^6$ viable cells/mL (for a total of $4\times10^4$ viable cells/well) into the CAR-T test wells and baseline control wells. Fifty μL of assay medium was added to the KILR LNcaP-KLK2 cell only (no cell death) wells. The contents of the wells were mixed gently and incubated for 15 min. (±5 min.) at 37° C., 5% $CO_2$, and humidified.

Upon completion of the incubation, 50 μL of target cells at $8\times10^4$ viable cells/mL were added to all assay wells (final $4\times10^3$ viable cells/well), which resulted in a final E:T ratio of 10:1. The contents of the wells were incubated at 37° C., 5% $CO_2$, and humidified for 20 hours (±2 hour). Upon completion of the co-culture incubation, assay plates were removed from the incubator and allowed to equilibrate at room temperature for 30 minutes (+/−5 minutes). The detection reagent was thawed and then equilibrated to room temperature for 30 minutes at the same time. In each assay, once equilibrated, 0.1% Triton X-100 (50 μL/well) was added to the total cell death control wells, followed by the addition of 100 μL of KILR® detection reagent to each well, and incubated while protected from light for 50 minutes (+/−5 minutes). The plate was read on a Molecular Devices Paradigm plate reader set for chemiluminescence after a 10 second shake.

The data are shown below in Table 8. The data showed a lot titration of sKLK2 protein demonstrating KLK2 blocking of KLK2 CAR-T DP killing of KILR LNcaP-KLK2 target cells ranging from 10-500 μg/mL.

Incubation times were aligned with those of Example 1 above. All other reagents were the same as those used in Example 1. Initial titration studies shown below in Table 8 indicate blocking of KLK2 CAR-T cells with the KLK2 soluble protein. (Internal, KL2W12.009).

TABLE 8

KLK2 CAR-T Titration Data

| Sample # | Test Method | Sample ID | % CAR-T Killing |
|---|---|---|---|
| 1 | Mock | SH20-KLK2-004-CAR-T with Mock | 96% |
| 2 | Soluble protein Blocking | SH20-KLK2-004-CAR-T w/125 ug/mL KLK2 soluble protein (500 mg/mL) | 107% |
| 3 | Soluble protein Blocking | SH20-KLK2-004-CAR-T w/100 ug/mL KLK2 soluble protein (500 mg/mL) | 111% |
| 4 | Soluble protein Blocking | SH20-KLK2-004-CAR-T w/75 ug/mL KLK2 soluble protein (500 mg/mL) | 106% |
| 5 | Soluble protein Blocking | SH20-KLK2-004-CAR-T w/50 ug/mL KLK2 soluble protein (500 mg/mL) | 96% |
| 6 | Soluble protein Blocking | SH20-KLK2-004-CAR-T w/25 ug/mL KLK2 soluble protein (500 mg/mL) | 79% |
| 7 | Soluble protein Blocking | SH20-KLK2-004-CAR-T w/12.5 ug/mL KLK2 soluble protein (500 mg/mL) | 68% |
| 8 | Soluble protein Blocking | SH20-KLK2-004-CAR-T w/2.5 ug/mL KLK2 soluble protein (500 mg/mL) | 49% |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate and are provided for description.

Patents, patent applications, publications, product descriptions, and protocols are cited throughout this application, the disclosures of which are incorporated herein by reference in their entireties for all purposes.

The invention claimed is:

1. An in vitro method for determining potency of a chimeric antigen receptor (CAR) T cell, the method comprising:
- a) in a test sample, contacting the CAR T cell with multiple myeloma target cells, wherein the multiple myeloma target cells express an antigen comprising a B-Cell maturation Antigen (BCMA) receptor which interacts with the CAR T cell,
- b) in a first control sample, contacting the CAR T cell with the multiple myeloma target cells, wherein (i) said contacting is conducted in the presence of an inhibitory molecule or (ii) the CAR T cell and/or the multiple myeloma target cells have been pre-incubated with the inhibitory molecule prior to said contacting, wherein the inhibitory molecule comprises a soluble extracellular domain of BCMA at a concentration of 50-400 μg/mL and inhibits the interaction between the CAR T cell and the multiple myeloma target cells,
- c) determining the amount of the multiple myeloma target cell death in the test sample,
- d) determining the amount of the multiple myeloma target cell death in the first control sample, and
- e) determining potency of the CAR T cell based on comparing the amount of the multiple myeloma target cell death determined in steps (c) and (d), wherein the contacting time, the amount of the CAR T cell and the amount of the multiple myeloma target cells are substantially the same in the test sample and the first control sample.

2. The method of claim 1, wherein the contacting steps (a) and (b) are performed simultaneously.

3. The method of claim 1, wherein the determining steps (c) and (d) are performed simultaneously.

4. The method of claim 1, wherein in step (b)(i) the CAR T cell and/or the multiple myeloma target cells have been pre-incubated with the inhibitory molecule prior to the contacting step.

5. The method of claim 1, wherein said method further comprises comparing the amount of the multiple myeloma target cell death determined in step (c) to the amount of the multiple myeloma target cell death determined in a second control sample, wherein the multiple myeloma target cells are incubated in the absence of the CAR T cell.

6. The method of claim 1, wherein said method further comprises comparing the amount of the multiple myeloma target cell death determined in step (c) to the amount of the multiple myeloma target cell death determined in a third control sample, wherein the multiple myeloma target cells are incubated in the absence of the CAR-T cell but in the presence of a detergent causing the multiple myeloma target cell death.

7. The method of claim 6, wherein the detergent is polyethylene glycol tert-octylphenyl ether.

8. The method of claim 1, wherein the multiple myeloma target cells produce a detectable reporter signal upon said multiple myeloma target cell death, and step (c) comprises determining the reporter signal in the test sample, step (d) comprises determining the reporter signal in the first control sample, and step (e) comprises comparing the reporter signals determined in steps (c) and (d).

9. The method of claim 8, wherein the reporter signal is luminescence.

10. The method of claim 8, wherein the reporter signal is fluorescence.

11. The method of claim 8, wherein the multiple myeloma target cells express a reporter protein that produces a signal when the multiple myeloma target cell undergoes cell death.

12. The method of claim 11, wherein the reporter protein is beta-galactosidase, luciferase, Green Fluorescent Protein (GFP), or a variant or derivative thereof.

13. The method of claim 1, wherein the inhibitory molecule specifically binds to the CAR T cell.

14. The method of claim 13, wherein the inhibitory molecule specifically binds to a region of the CAR T cell that specifically binds to the antigen expressed on the multiple myeloma target cells.

15. The method of claim 1, wherein the multiple myeloma target cells are MM-1R cells.

16. The method of claim 1, wherein the method is conducted in a high throughput format.

* * * * *